United States Patent
Suh et al.

(10) Patent No.: US 6,386,865 B1
(45) Date of Patent: May 14, 2002

(54) SYSTEM FOR FABRICATION OF INDIRECT DENTAL RESTORATIVES

(75) Inventors: Byoung I. Suh, Oak Brook, IL (US); Patrick L. Roetzer, Benicia, CA (US); Rich Nagel, West Chicago, IL (US)

(73) Assignee: Bisco Inc., Schaumburg, IL (US)

( * ) Notice: Subject to any disclaimer, the term of this patent is extended or adjusted under 35 U.S.C. 154(b) by 0 days.

(21) Appl. No.: 09/371,737

(22) Filed: Aug. 10, 1999

Related U.S. Application Data

(63) Continuation-in-part of application No. PCT/US98/02271, filed on Feb. 13, 1998.
(60) Provisional application No. 60/039,731, filed on Feb. 14, 1997, and provisional application No. 60/067,666, filed on Dec. 5, 1997.

(51) Int. Cl.[7] .............................. A61C 1/00; A61C 5/10
(52) U.S. Cl. ........................... 433/27; 433/223; 264/16
(58) Field of Search ................................. 433/213, 218, 433/223, 214, 27; 264/16, 17, 18, 19, 20

(56) References Cited

U.S. PATENT DOCUMENTS

| | | | | |
|---|---|---|---|---|
| 2,423,330 A | * | 7/1947 | Levine | 264/17 |
| 3,001,240 A | * | 9/1961 | Emerick | 264/17 |
| 3,905,106 A | * | 9/1975 | Costa et al. | 433/213 |
| 4,571,188 A | | 2/1986 | Hamilton | 433/226 |
| 4,865,546 A | * | 9/1989 | Naylor | 433/213 |
| 5,000,687 A | | 3/1991 | Yarovesky et al. | 433/180 |
| 5,040,964 A | * | 8/1991 | Oppawsky et al. | 264/16 |
| 5,104,591 A | * | 4/1992 | Masuhara et al. | 264/16 |
| 5,348,475 A | * | 9/1994 | Waknine et al. | 264/16 |
| 5,667,386 A | * | 9/1997 | Black et al. | 433/213 |

FOREIGN PATENT DOCUMENTS

| | | |
|---|---|---|
| DE | 33 30 853 A1 | 3/1985 |
| DE | 40 05 570 A1 | 8/1991 |
| EP | 0 511 554 A1 | 4/1992 |
| EP | 0 581 226 A3 | 2/1994 |
| EP | 0 581 226 A2 | 2/1994 |
| EP | 0 742 001 A2 | 11/1996 |

OTHER PUBLICATIONS belleGlass™ HP Heat & Pressure Processed Polymer–Glass Dual Cure Restorative Quick Reference Guide, 6 pages (undated).

(List continued on next page.)

Primary Examiner—Todd E. Manahan
(74) Attorney, Agent, or Firm—Marshall, O'Toole, Gerstein, Murray & Borun

(57) ABSTRACT

A process for the fabrication of indirect dental restoratives includes the making of a first, pre-operative impression of a tooth to be restored using a first polyvinyl silicone (PVS) material disposed in a clear tray, followed by the preparation of the tooth. A second, final post-operative impression of the tooth is taken utilizing a second PVS material. A tooth model is then made by pouring a low viscosity and suitably rigid, third PVS material into the final impression. Prior to the complete setting of the low viscosity PVS material, a higher viscosity, fourth PVS material is applied onto the model PVS material to form a completed model with base. The model is then fitted into the pre-operative impression matrix made from the first PVS material. Layers of composite are packed onto the impression in the clear matrix. The model (with attached base) is then inserted into the composite disposed in the first PVS material and the resulting matrix is placed in a single apparatus for conducting both light and heat cure of the dental composite. The apparatus can utilize a thermister disposed in a composite material, the thermister/composite assembly being disposed in a curing chamber of the apparatus and connected to a control device which controls a heat lamp also disposed in the apparatus. Curing of the dental composite is performed by heating until, for example, the thermister reaches a selected temperature.

36 Claims, 8 Drawing Sheets

OTHER PUBLICATIONS belleGlass™ HP *The New Class In Restorative Dentistry* brochure, 8 pages (undated).

Sculpture™ FibreKor™ Restorative System *The Esthetics Of Porcelain & The Strength Of Metal* brochure, 1997 Jeneric/Pentron Incorporated, 6 pages.

Sculpture™ FibreKor™ product profile, Cure–Lite™ plus and Sculpture™ Pressure Bowl, Jeneric/Pentron Incorporated, Jun. 1997, 1 page.

Jeneric/Pentron Incorporated SAA–V116–NQ Vacuum Pump product description, Jul. 1997, 1 page.

Targis™ Ceromer System tooth restoration system product description, Stern Empire Dental Laboratory, 2 pages (undated).

Targis™ Ceromer System tooth restoration system product description, Recigno Laboratories, Inc., 2 pages (undated).

Targis™/Vectris™ Durabridge® Natural Restoration product description, Recigno Laboratories, Inc., 2 pages (undated).

The Targis™ System brochure, "*This revolutionary metal- -free restorative system is changing the dental world!*" Ivoclar Williams, Ivoclar North America, Inc., 16 pages (undated).

The Targis™ System brochure, "*Join The Esthetic Revolution*", Ivoclar Williams, Ivoclar North America, Inc., 8 pages (undated).

Right On Targis! Revolutionary Targis™ Ceromer System product description, Ivoclar Williams, 1996 Ivoclar North America, Inc., 3 pages.

\* cited by examiner

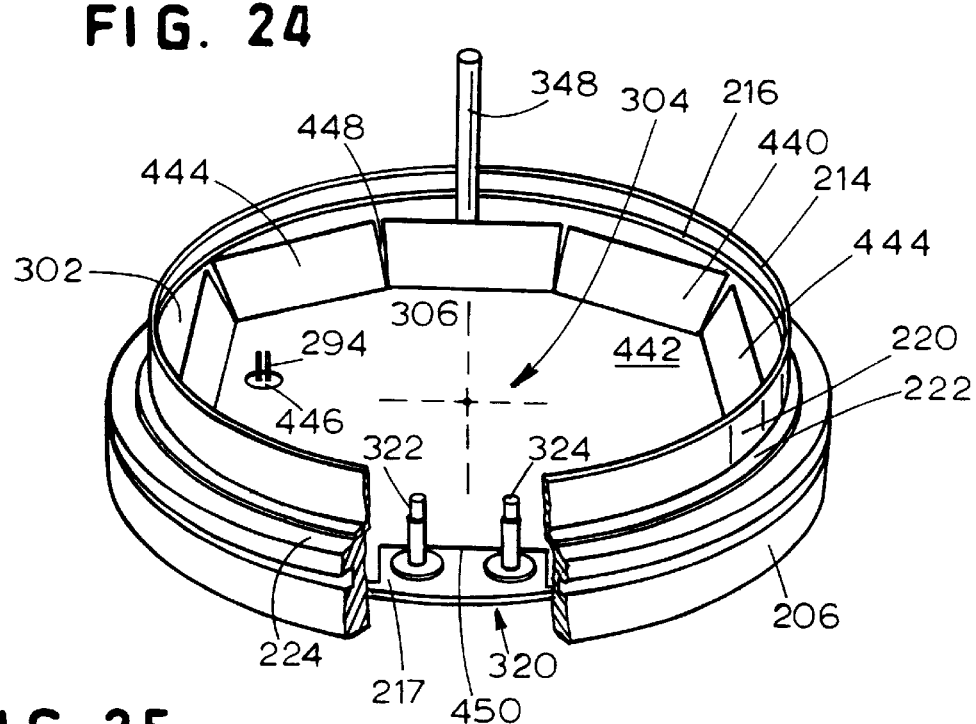
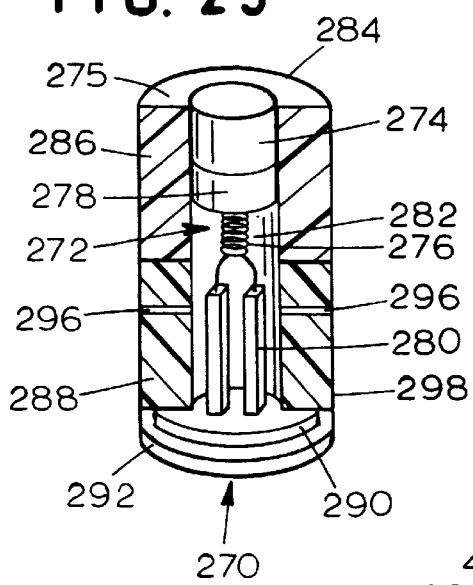
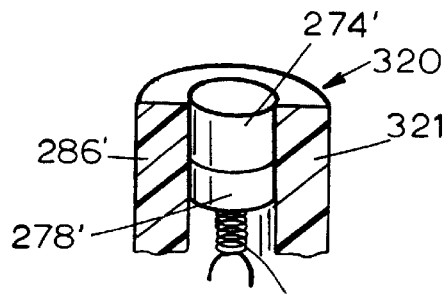
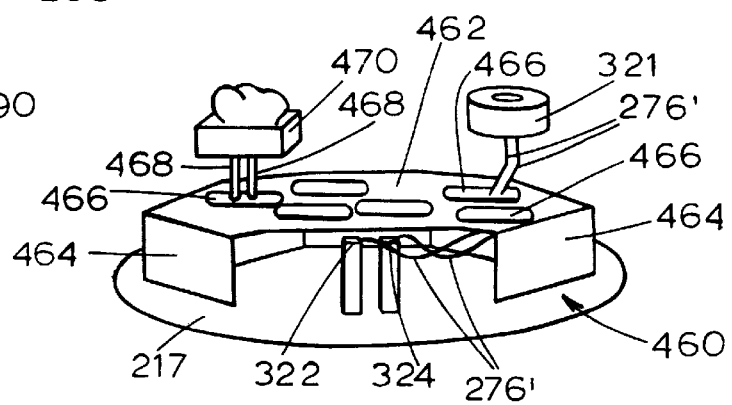

SYSTEM FOR FABRICATION OF INDIRECT DENTAL RESTORATIVES

CROSS-REFERENCE TO RELATED APPLICATIONS

This is a continuation-in-part application of International Application No. PCT/US98/02271 filed Feb. 13, 1998, which claims the priority benefit under 35 U.S.C. § 119(e) of U.S. provisional application Serial No. 60/039,731, filed Feb. 14, 1997, and U.S. provisional application Serial No. 60/067,666, filed Dec. 5, 1997.

BACKGROUND OF THE INVENTION

1. Field of the Invention

This invention relates generally to indirect dental restorations. Specifically, the present invention relates to a system for fabrication of indirect restoratives utilizing polymer composites which may be performed during a single dental office visit or in the dental lab by a technician.

2. Brief Description of Related Technology

For centuries, restorative dentistry has been performed utilizing the lost wax technique wherein gypsum dies created from impressions are made of the prepared teeth. Gypsum-containing setting materials require a certain amount of time to set up. Setting time of the restoration materials can be decreased, but at the peril of accuracy problems. Gypsum models also require mounting on articulators, utilizing plaster, requiring a certain amount of setting time to mount a model. Thus, regardless of the impression material used, the setting time required by gypsum-containing materials requires the dentist to make a second appointment with a patient to affix a permanent restoration.

An other problem with using gypsum-containing dies is that certain restorative materials tend to adhere to the gypsum, regardless of the separator material applied to the dies One of the reasons for this is that although separator materials may be prepared which work for most materials, it is undesirable to coat margin areas on the die with the separator material for fear of creating a space in this area in the finished restoration. Thus, technicians have expected to have die models chipped at the margins during fabrication This dilemma has been solved by duplicating the master model for fabrication purposes, necessitating an additional step which may create more error in material shrinkage/expansion parameters. Each time a master model is duplicated, accuracy is at risk. Another problem with duplicating the master model is that the master model must still be used to fit the restoration, creating the risk of wearing and chipping of the master model. Regardless of these problems, this technique, which requires at least two patient office visits, is still being utilized in the dental industry.

One alternative to gypsum dies has been to utilize a light-curable polymer composite inlay fabricated in the patient's mouth, which is then removed from the mouth for final curing and then cemented in the patient's mouth, during a single office visit. Problems with such a system include the fact that the fabrication field is not always free of saliva and blood, which can interfere with the setting of the composite. Another problem with such a system is that the occlusion may be overly high because the patient is not able to bite into the setting composite to form a functionally generated path-type restoration. Contacts are also a problem with such a system. The contacts must sometimes be added after removal of the composite from the mouth because, for example, the stainless steel band on a retainer may interfere and create an open interproximal contact.

Furthermore, even if the fabrication field is dry (free of blood and saliva), the contact adequate, and the occlusion easy to manipulate, the composite utilized in such a system may have a tendency to lock into slight undercuts in a prepared tooth. If the light-curable composite set inlay hardens in such tooth undercuts, the restoration cannot be removed for final curing. Also, since the composite in the proximal box area is tacky and soft because light cannot reach it, removal of the restoration may result in breakage or deformation of the composite pattern, particularly in large, complex restorations. One way in which this problem has been solved is to place the tip of a paper clip in the central pit area of the restoration so that the clip sticks like a sprue pin in a wax pattern, and thus provides a way to vertically remove the restoration.

Further problems with such a system include the formation of an overly dry surface after light cure outside of the mouth, inadequate cementation of the finished restoration onto the dentin and enamel bonded prepared tooth, and the previous lack of chair-side sand blasting technology, The desire for chair-side availability of restorations also has led to the development of milling machines. An early machine included a copy-key device. The system included taking a pre-operative impression, preparing the tooth, and taking a post-operative impression with a stiff material. A stylus of the milling machine followed the contour of the intaglio surface of the post-operative impression, which was transferred to a milling arm, which cut the shape into a block of feldspathic porcelain. The occlusion was cut into the opposite side of the restoration by following the occlusal morphology of the poured pre-operative model with the stylus. Problems with this system included the difficulty in keeping the impression immobile on a pedestal while the stylus tracked over the surface of the impression. Furthermore, the cost of the milling machine prohibited many dental offices from utilizing this system.

Improved milling machines utilizing CAD/CAM technology are available, but are considered cost-prohibitive by many. Also, polishing is required for any porcelain restoration. A further draw-back is the monochromaticity of the porcelain.

The monochromaticity problem may be solved by replacing porcelain restoratives with those made from a variety of polymer composites. A current trend is to prepare permanent dental restorations from composite materials made by free-radical polymerization of methacrylate functionalized monomers or oligomers. The formed highly viscous polymerization products typically are cured by light, (e.g., by a visible light source) or by heat, or by a "dual" light- and self-cure. It also is known that traditional light-cure, self-cure and "dual" light/self cure composites may be further polymerized by exposure to heat.

In some instances, the presence of oxygen has been found to inhibit the light curing of free-radical initiated chemical systems. This oxygen inhibition is noticed on a cured surface as occlusal haziness or tackiness. To avoid these aesthetic flaws, some processes, such as the one disclosed in Yarovesky et al., U.S. Pat. No 5,000,687 teach light cure under an inert nitrogen atmosphere. Dual cure (i.e., light/heat) has been found to impart good post-cure strength to the composite product.

Conventional processes for fabricating restorative dental implants have proven quite expensive, and time consuming. Currently, dentists must send single and multiple unit restorations to off-site dental laboratories. These laboratories are the only source capable of manufacturing dental implants having strength, color, and other aesthetic qualities demanded by patients and their dentists.

Currently, the overall process to provide a patient with a final, permanent restoration requires the patient to make at least two separate dental visits. In the first visit, the dentist typically prepares a subject tooth, prepares and cements a temporary restoration, removes excess cement, checks for temporary occlusion, and prepares a final impression which is then sent to a dental laboratory where a permanent restoration is made. In the second visit, the dentist removes the temporary restoration, removes residual temporary cement, trial-fits the lab-fabricated permanent restoration, checks margins and occlusal harmony with opposing teeth, and then cements the permanent restoration.

There are numerous disadvantages of the current multiple-visit procedure. One notable disadvantage is the inconvenience to the patient in having to undergo an interim procedure where a temporary restoration is affixed and, subsequently, undergoing another procedure to remove the temporary restoration and then to affix the permanent restoration. Each visit may require anesthetizing. Furthermore, each visit requires the patient to take time away from work or home. Another disadvantage of the current multiple-visit procedure is the added cost to the dentist, such as the cost in foregoing the opportunity to attend to another patient, and in the added costs in preparing a dental operatory. Often times the preparations required for the added visits are not billable. The current multiple-visit procedures are also uneconomical, especially considering that many dentists' offices, such as those associated with managed care programs, are staffed with qualified dental assistants who could be trained to fabricate permanent restorations having superior integrity and aesthetic qualities.

A known process for manufacturing a permanent dental restoration which can be completed in a dentist's office during one patient visit, includes the use of a polyvinyl silicone (PVS) die in lieu of the traditional gypsum die. Instead of pouring a post-operative impression with gypsum stone, PVS having a high filler content is utilized. Such a PVS material does not stick to either alginate or hydrocolloid and also does not distort the material in its set. PVS impressions may be injected with this material if a silicone mold release agent is first sprayed into the post-operative impression In addition to excellent marginal accuracy, dies made from PVS materials allow for easy composite removal after polymerization of the composite restorative.

A variety of composites, including self-cure, light cure and dual cure (light/self cure) may be packed into these dies and cured at high oven temperatures without degradation of the PVS material. The composite material may be added in layers, fully curing each layer by light in an oxygen environment prior to the addition of a subsequent layer, and optionally, final curing the composite in an oven for a few minutes at about 250° F. (121° C.). Oven temperatures of up to 270° F. do not affect the integrity of the die material thereby allowing multiple restorations to be done on the same die. Advantages of such a system include the fact that shrinkage of the restorative occurs outside of the mouth and occlusion can be ground on the bench rather than in the mouth.

However, formed restorations made according to such a procedure have lacked the strength, integrity and aesthetic qualities characteristic of the restorations made in off-site dental laboratories. Also, the progressive loading of material requires that additional cosmetic material be added over the formed restoration to increase its occlusal loading. The occlusal loading is necessary to minimize the effects of haziness thought to be formed by light curing in the presence of oxygen. Another drawback is the oxygen inhibited layer that forms during polymerization, resulting in a tacky relatively soft surface of the restorative.

Thus, it remains desirable to provide a system for preparing dental restoratives of improved strength and aesthetic qualities which can be made in a dentist's office during a single patient visit without the aid of the highly skilled technicians of dental laboratories.

SUMMARY OF THE INVENTION

It is an object of the invention to overcome one or more of the problems described above.

In a process according to the invention, a first, pre-operative impression of a tooth to be restored is taken using a first polyvinyl silicone (PVS) material disposed in a clear tray, followed by the preparation of the tooth. A second, final post-operative impression of the tooth is taken utilizing a second PVS material. A tooth model is then made by pouring a low viscosity and suitably rigid, third PVS material into the final impression. Prior to the complete setting of the low viscosity PVS material, a higher viscosity, fourth PVS material is applied onto the model PVS material to form a completed model with base. The model is then fitted into the pre-operative impression matrix made from the first PVS material. Layers of composite are packed onto the impression in the clear matrix. The model (with attached base) is then inserted into the composite disposed in the first PVS material and the resulting matrix is placed in a single apparatus for conducting both light and heat cure of the dental composite.

Also according to the invention are curing apparatus and methods utilizing the apparatus to prepare a dental restorative. The apparatus can utilize a thermister disposed in a composite material, the thermister/composite assembly being disposed in a curing chamber of the apparatus and connected to a control device which controls a heat lamp also disposed in the apparatus. Curing of the dental composite is performed by heating until, for example, the thermister reaches a selected temperature.

Other objects and advantages of the invention may become apparent to those skilled in the art from a review of the following detailed description, taken in conjunction with the drawings and appended claims.

BRIEF DESCRIPTION OF THE DRAWINGS

The accompanying drawings illustrate the invention. In such drawings:

FIG. 24 is a partial and enlarged perspective view of a portion of the apparatus shown in FIG. 21.

FIG. 25 is a cross-sectional view of a sensor according to the invention utilized in the apparatus shown in FIG. 21.

FIG. 26 is a cross-sectional view of a second sensor according to the invention optionally utilized in the apparatus shown in FIG. 21

FIG. 27 is a perspective view of a tray according to the invention for use with the apparatus shown in FIG. 21 and shown with a dental restorative mounted thereon.

DETAILED DESCRIPTION OF THE INVENTION

Figure 1:
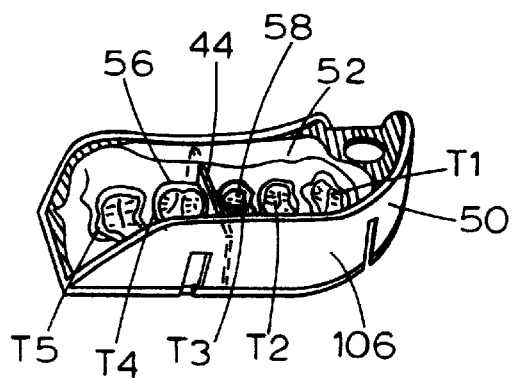
FIG. 1 is a perspective view of a tray containing a material for use in forming a first impression according to a process of the invention.

By processes according to the invention, the direct and indirect technology of lab quality is brought to the average dentist. According to the invention, a dentist can take a pre-operative impression with a high definition, heat resistant, clear polyvinyl silicone matrix material bound to a clear tray which allows for the accurate creation of single or multiple adjacent crowns, onlays, inlays or bridges.

According to a process of the invention, a dentist first takes a pre-operative impression of the tooth to be restored using a transparent perforated impression tray filled with a clear polyvinyl silicone impression material. This clear matrix will be used to create the final morphology and surface characteristics of the final restoration.

Next the subject tooth is prepared and a final impression is taken using a PVS impression material (monophase material). If an articulated model is to be used, an impression of the opposing arch also is taken at this time. A suitable release agent is then applied to the dry impression.

A tooth model is then made by pouring a low viscosity and suitably rigid PVS material into the final impression (and opposing impression if an articulator is to be used). A higher viscosity PVS material is then applied onto the model PVS material. It is noted that the higher viscosity PVS material may be applied prior to the complete setting of the low viscosity PVS material, but this is not required. In fact, the model PVS material may set up quickly, and thus be set by the time the higher viscosity PVS material is applied. There may even be a substantial time lapse (e.g., twenty-four hours or more) between the preparation of the model and the application of the higher viscosity PVS material. When built up, more of this base material is introduced into a plastic index tray to form the completed model with base.

The model is then fitted into the clear pre-operative impression matrix. A vertical trough (also called a vent or swale) is made on the buccal and lingual sides of the model opposite the middle of the prepared tooth to allow excess composite material to flow away from the final restoration.

The model is removed from the matrix and vertical troughs are then extended to a location near the margins of the restoration and a horizontal trough is added through (e.g., approximately perpendicular to) the vertical trough. This intersection will lock the composite material onto the model should more composite be required.

Layers of composite are then packed onto the impression in the clear matrix. Customizing the final shade of the restoration may be done at this time by layering the appropriate shades of composite, beginning with the occlusal and working gingivally. A central cavity is created as the composite is packed. This cavity will act as a path of insertion for the die when it is fully occluded with the clear matrix model.

Before inserting the die into the clear matrix, composite is packed around the margins, gingival and pulpal regions of the preparation. This will ensure that margins are covered with composite.

The model (with attached base) is then inserted into the composite-containing clear matrix slowly to allow for excess composite to flow down the troughs. Once fully seated into the clear matrix, the model is secured to the matrix, preferably with a self-locking strip. Also preferably, a v-shaped notch is placed on the bottom of the base using a lab knife, before pressing the matrix together. This allows the tie to go under and through the base, thus allowing the base to rest flush (i.e., be flat) against a heating tray in the curing device.

The base/model matrix is then placed in a single apparatus for conducting both light and heat cure of the dental composite. If desired, this provides for dual (heat/light) curing in an oxygen-free, pressurized environment. The term "oxygen-free" as used hereinafter is intended to mean an environment substantially free of molecular oxygen, such as an environment comprising an inert gas (e.g., nitrogen, argon etc.) or steam or water.

Upon completion of the curing cycle, the clear matrix is separated from the base model, with the restoration remaining intact on the model due to the locking nature of the troughs.

The finished restorative may then be finished and polished.

The foregoing procedure can be run with heat, light or traditional dual (light/self) composites. "Light-cure-only" composites can be used in the current invention but without the advantages of the heat cure. Also, "heat-cure-only" composites can be used in the current invention but without the advantages of light cure. Preferably, processes and methods of the invention include the use of a dual light- and heat-cure composite. Thus it is noted that as further described herein, the term "dual" cure is broad enough to include both light/self cure, light/heat cure, and heat/self cure composites. Furthermore, triple-cured composites (light, self and heat) have been used in processes and apparatus according to the invention.

Two component systems also can also be used, however, a single component system with a proper thermal initiator is a preferred system for the current invention. Such single component, dual (light/heat) cure composites exhibit good shelf life at room temperature since the initiation temperature of the thermal initiator is preferably above room temperature.

Dual cure (light/heat) composite materials for use in the process of this invention comprise a resin, at least one inorganic filler, a polymerization reaction initiator to initiate light cure, an amine accelerator, at least one thermal catalyst to initiate thermal cure, pigments as needed for coloration, and stabilizers. Suitable components of the resin include at least one reactive methacrylate functionalized monomer or oligomer, selected from the group comprising 2-hydroxyethyl methacrylate (HEMA), ethylene glycol dimethacrylate (EGDMA), diethyleneglycol dimethacrylate (DEGDMA), triethylene glycol dimethacrylate (TEGDMA), tetrahydrofurftiryl methacrylate, trimethylolpropane trimethacrylate (TMPTMA), analogous acrylates or methacrylates, 2,2-bis[4(2-hydroxy-3-methacryloxypropoxy)phenyl]propane (bis-GMA), urethane dimethacrylate (UDMA), diphenyl sulfone dimethacrylate, and similarly functionalized monomers or oligomers. Monomers and oligomers disclosed in Qian et al., U.S. Pat. No. 5,658,963, may be used in the present invention, and are incorporated by reference herein. The monomer also may be polytetramethyleneglycol dimethacrylate (PTMGDMA) and similar materials of varying molecular weight.

Suitable inorganic fillers comprising the dual cure composites for use in the process of this invention include at least one, and more preferably mixtures of two to four of the materials, including the following: barium aluminum silicate, barium oxide, lithium aluminum silicate, strontium, lanthanum, tantalum, glass, quartz, silica, fused silica, colloidal silica, alumina, zirconia, tin oxide, and the like. Preferably, the fillers are silanated to facilitate bonding with the components of the resin. Filler particle size may vary from 0.005 to 15 microns in diameter. Preferred fillers may have particle sizes from about 0.01 to 13 microns.

Suitable polymerization reaction initiators for visible light curing include camphorquinone, benzil, biacetyl, 9,10-phenanthrenequinone, and naphthoquinone. Preferably, the polymerization reaction initiator is an alpha diketone, such as camphorquinone.

Suitable amine accelerators include tripropylamine, N-alkyldialkanolamine, tryalkanolamine, and acrylate or methacrylate derivatives of the same or similar amines. Preferred amine accelerators are dimethyl ethyl amine and ethyl 4-dimethylamino benzoate. More preferably the amine accelerator is ethyl 4-dimethylamino benzoate. Polymerization reaction initiators and amine accelerators disclosed in Qian et al., U.S. Pat. No. 5,658,963, also may be used in the present invention, and are incorporated by reference herein.

Suitable thermal catalysts include benzoyl peroxide, t-butyl perbenzoate, or 1,1-di(tert-butylperoxy)-3,3,5-trimethylcyclohexane. Preferred thermal catalysts are t-butyl perbenzoate or 1,1-di(tert-butylperoxy)-3,3,5-trimethylcyclohexane. More preferably the thermal catalyst is tert-butyl perbenzoate.

Additional adjuvants, such as pigments, tints, and stabilizers, such as hydroquinone monomethyl ether or butylated hydroxy toluene (BHT), may be added as needed to obtain necessary and desired strength, shelf-life, and aesthetic characteristics. Other adjuvants, such as surfactants, fibers for reinforcement, fluoride release chemicals, and thickening agents, also may be added.

The weight ratio of fillers to resin is typically in the range of about 85:15 to about 40:60, preferably in the range of about 80:20 to about 50:50, and most preferably in the range of about 80:20 to about 65:35.

Strength tests were performed on some of the dental composite compositions A, B, and C utilized according to the invention. Each of the formulas for compositions A, B, and C disclosed in Tables I and II included the same resin mixture and a different filler (each of the composites being 76% filled). The resin portion of each of the compositions is disclosed in the following Table I.

TABLE I

| Resin | |
|---|---|
| Resin | Weight Percent of total resin/filler mixture |
| Bis-GMA | 9.90 |
| Tri-EDMA | 8.00 |
| UDMA | 0.48 |
| T-butyl Perbenzoate | 0.48 |
| UV 3000 | 0.48 |
| EDMAB | 0.30 |
| MEHQ | (trace) |

The fillers utilized in each of the formulas are set forth in the following Table II.

TABLE II

| Fillers | | | |
|---|---|---|---|
| Component | Formula A | Formula B | Formula C |
| Barium Glass Schott | 52.0 | 52.0 | 44.4 |
| OX-50 (silica) | 3.8 | 3.8 | 3.8 |
| R972 | 3.8 | 3.8 | 3.8 |
| Tints | 1.2 | 1.2 | 1.2 |
| T-4000 (strontium) | 15.2 | | |
| Barium Glass Regular | | 15.2 | |
| Strontium Glass RWG | | | 22.8 |

Table III, shows the typical strength improvement due to thermal/light cure in a process according to the invention, of each of the three compositions A, B, and C.

TABLE III

Diametral Strength (Mega Pascals)

| Type of Cure | Formula A | Formula B | Formula C |
|---|---|---|---|
| Light Cure Only | 54.6 (+/−2.2) | 52.7 (+/−2.9) | 55.7 (+/−3.3) |
| Light Cure and Heat (7.5 min., 125° C.) | 59.6 (+/−6.3) | 62.5 (+/−3.6) | 63.6 (+/−3.6) |

Impression materials utilized according to processes of the invention are preferably polyvinyl siloxane materials. The following materials may be used:

For the clear polyvinyl siloxane impression material (PVS), preferably CLEAR MOLD PVS (Hyunjae Corp., New Milford, Conn.) is utilized. Also MEMOSIL C.D.® PVS (Kulzer, Irvine, Calif. (item #171-1474, Henry Shein, Port Washington, N.Y.)) may be used. However, this material is not as transparent as CLEAR MOLD PVS.

For the PVS final impression material, MONOPHASE F.I PVS (Hyunjae Corp., Dan Cho) or HYDROSIL XT® PVS (Caulk (item #222-2993, Henry Shein)) may be used. Alternative final impression materials include hydrocolloids such as the reversible VERSATOLE™ material (Henry Shein (item #100-3655) or irreversible alginates such as SYSTEM 2™ ACCU-GEL material (two-part system impression utilizing a tray material with a syringeable material by ACCU-DENT; because these materials contain up to 85% water in their composition, they may not be desirable due to their limited dimension stability).

Polyethers such as IMPREGUM F material (manufactured by Premier and sold by Henry Shein; item #378-1718) might be used as an alternative impression material. However, such materials polymerize very slowly and do not go to completion for several hours. A minimum of thirty minutes is suggested between impression time and pour-up which may defeat the time savings of processes according to the invention. Furthermore, such polyethers do not appear to be compatible with the preferred PVS materials used according to the invention.

For the PVS die material, QUICK DIE PVS (Hyunjae Corp.; supplied by Millennium Dental International, Gaylordsville, Conn.) or MACH 2® PVS (Parkell, Farmington, N.Y.; Stock #S433-SM) may be used. The PVS base material may be BLUE BASE PVS (Hyunjae Corp.) or SUPER-FAST BLU-MOUSSE® PVS (Parkell; stock #S457-SM).

Syringing equipment used in processes of the invention include an impression gun called an "extruder" or a "dispenser" (Henry Shein item #100-0956); gun static mixing tips (Henry Shein item #100-2459); intraoral tip (a reduction tip for mixing tip) (Henry Shein item #100-9634); and a Standard Impression Syringe (Centrix (Henry Shein item #163-6496)).

Impression trays (perforated) for use in processes of the invention include the following Clear impression trays for clear PVS:

a. SUPER-DENT® Crystal Clear trays (Darby Dental Supply Co., Rockville N.Y.):
 1. Anterior quadrant tray (stock #981-2264);
 2. Lower left/upper right quadrant tray (stock #981-2260);
 3. Lower right/upper left quadrant tray (stock #981-2262);

Full arch clear trays are also available under SUPER-DENT® name.

Final impression trays are sold under the TRAY-AWAYS™ name (Bosworth (sold by Henry Shein Dental)) and include:

1. Anterior quadrant-(Henry Shein item #250-2483);
2. Upper right/lower left (Henry Shein item #250-1855);
3. Lower right/upper left (Henry Shein item #250-2320).

An index tray for mounting the base/impression matrix is sold under the trade name DIE-MAKER ARTICULATORS (Item #0020; Accu-Bite Dental Supply, Williamson, Mich.).

The following tables (IV–VII) provide physical properties for polyvinyl siloxane materials, each supplied by the Hyunjae Corporation, New Milford, Conn., for use in processes according to the invention.

TABLE IV

Physical Properties of PVS Clear[1]

| Property | Specification |
|---|---|
| Work Time | 80–110 Seconds |
| Set Time (ambient) | 5–6 Minutes |
| Set Time (oral) | 4–5 Minutes |
| Dimensional Stability | Less than 0.2% |
| Viscosity | 500,000–600,000 cps |
| Durometer | 48–52 Shore A |

[1] Polyvinyl siloxane utilized for pre-operative first impression.

TABLE V

Physical Properties of PVS Monophase[1]

| Property | Specification |
|---|---|
| Work Time | 80–100 Seconds |
| Set Time (ambient) | 7–10 Minutes |
| Set Time (oral) | 4.0–5.5 Minutes |
| Dimensional Stability | Less than 0.2% |
| Viscosity | 400,000–450,000 cps[2] |
| Durometer | 48–52 Shore A |

[1] Polyvinyl siloxane utilized for post-operative final impression.
[2] Centipoise.

TABLE VI

Physical Properties of PVS Die[1]

| Property | Specification |
|---|---|
| Work Time | 45–90 Seconds |
| Set Time (ambient) | 90–150 Seconds |
| Dimensional Stability | Less than 0.2% |
| Viscosity | 20,000–30,000 cps |
| Durometer | 80–85 Shore A |

[1] Polyvinyl siloxane utilized to prepare tooth model in final impression.

TABLE VII

Physical Properties of PVS Base[1]

| Property | Specification |
|---|---|
| Work Time | 60–130 Seconds |
| Set Time (ambient) | 4.5–5.5 Minutes |
| Set Time (oral) | 2.5–4.5 Minutes |
| Dimensional Stability | Less than 0.2% |
| Viscosity | 350,000–450,000 cps |
| Durometer | 70–75 Shore A |

[1] Polyvinyl siloxane utilized to prepare base for tooth model.

The following table provides the specific properties of PVS utilized in a test run of a process according to the invention.

TABLE VIII

Physical Properties of Test

| Name | Viscosity[1] | Work Time[2] | Set Time[3] | Set Time[4] | Durometer |
|---|---|---|---|---|---|
| PVS Clear[5] | 550,000 | 120 | | 4 | 50 Shore A |
| PVS Mono-Phase[6] | 425,000 | 120 | | 4 | 50 Shore A |
| PVS Die[7] | 24,000 | 45 | 90 | | 84 Shore A |
| PVS Base[8] | 400,000 | 60 | 180 | | 74 Shore A |

[1] In centipoise.
[2] In seconds.
[3] Ambient - in seconds.
[4] Oral - in minutes.
[5] Polyvinyl siloxane utilized for pre-operative first impression.
[6] Polyvinyl siloxane utilized for post-operative final impression.
[7] Polyvinyl siloxane utilized to prepare tooth model in final impression.
[8] Polyvinyl siloxane utilized to prepare base for tooth model.

Figure 2:
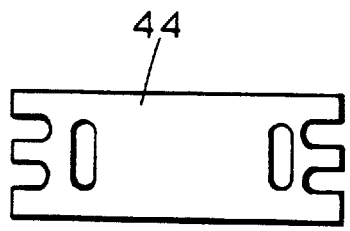
FIG. 2 is a perspective view of a separator for use in a process according to the invention.

According to an aspect of the process of the invention and with reference to FIGS. 1 and 2, any two adjacent teeth that are to be fitted with dental restoratives (e.g., crowns) require the placement of an interproximal separator 44 between each other to avoid a subsequent fusion of the crowns at adjacent interproximal contours during final composite curing. Generally, the interproximal separator 44 is any thin flat material capable of separating two adjacent teeth. For example, the interproximal separator 44 for use according to the process of this invention may be a thin (e.g., 0.001 inch thick) stainless steel plate. A hemostat may be used to insert the separator 44 between the subject teeth. If necessary, a sawing motion may allow easy passage of the separator even in tight contacts. Such separators are inserted vertically and touch the gingival tooth area (i.e., that portion of the tooth and gum where the tooth comes into contact with the gums). If the contacts are loose and the separators are unstable they can be stabilized by injecting a flowable, light-curable, polymer resin into the gap between the contacts and light curing the separator into place. Preferably, the separator is rigidly fixed in place such that material used to form a model of the subject teeth does not unseat the separator.

According to a process of the invention a first impression of the subject teeth is prepared. With reference to FIG. 1, a tray 50 is filled with a matrix material 52. The tray 50 is preferably a modified clear plastic tray and the matrix material 52 is preferably a polyvinyl silicone (PVS). More preferably the matrix material 52 is a clear, colorless, heat resistant PVS, such as a polyvinyl siloxane material disclosed as "PVS Clear" in Table IV. The filled tray 50 is then placed against the subject teeth T1–T5 (e.g., the damaged tooth and the teeth immediately adjacent the damaged tooth in the same dental arch) and maintained in this position with pressure for about 1 to about 5 minutes, or for a period of time sufficient to allow the matrix material 52 to gel. The tray 50 and gelled matrix material 52 are then removed from around the subject teeth T1–T5, leaving in the gelled matrix material an impression (e.g., near perfect negative) of the subject teeth T1–T5. In other words, the gelled matrix material has been impressed with cavities 56 and 58 formed in the subject teeth T3 and T4.

Generally, it is difficult to attach a dental restorative to a tooth having jagged edges or protrusions because cement or luting agents are difficult to apply to these surfaces. Thus, it is desirable to eliminate the undesired contours and protrusions of the tooth prior to affixing a dental restorative by shaping, contouring, and/or grinding the tooth such that it contains a surface suitable for receiving the dental restorative. This is known as "reducing" a tooth.

Once the subject tooth (here, tooth T3 and tooth T4) has been reduced, a second impression (also referred hereafter as a "final impression") is prepared. This second impression is prepared in a manner very similar to the preparation of the first impression described above. Generally, a tray, preferably a modified clear plastic tray, is filled with a matrix material, preferably a polyvinyl silicone (PVS), and most preferably a polyvinyl siloxane identified as "PVS Monophase" in Table V. The PVS filled tray is then placed against the reduced, subject teeth and maintained in this position with pressure for about one to about five minutes, or for a period of time sufficient to allow the matrix material to gel. The tray and gelled matrix material are then removed from around the subject teeth leaving in the gelled matrix material an impression (e.g., near perfect negative) of the reduced, subject tooth and the immediately adjacent teeth of the same dental arch. In other words, the gelled matrix material has been impressed with cavities formed by the reduced, subject tooth and teeth adjacent thereto.

A silicone mold release agent is then sprayed onto the impression. A currently preferred mold release agent is sold under the trade name SILICONE MOLD RELEASE by Huron Technologies, Ann Arbor, Mich. The preferred mold release agent is a composition which is a mixture of 50%–60% hexane, 15%–20% aliphatic hydrocarbons, 8%–10% propane and 1%–5% isobutane. This mold release agent is biodegradable and can be used on materials heated up to about 400 degrees F.

Next, a high density, low viscosity, highly filled PVS material (referred to hereafter as "PVS die 72"), preferably a polyvinyl siloxane disclosed in Table VI, is placed (i.e., injected) into the cavity formed in the second impression's matrix material by the subject teeth. This particular PVS material is used in conjunction with another, more flexible PVS material (referred hereafter as "PVS base 74"), preferably a polyvinyl siloxane material disclosed as "PVS Base" in Table VII. The PVS base 74 material has an even higher viscosity and is used to form an indexed base using a base former/articulator tray 76 having a base former portion 78 which includes index trays 79 (shown in FIGS. 3 and 4).

The "PVS die" and "PVS base" materials according to the invention are advantageous as they work together to form a rigid tooth model and a more flexible base attached to the tooth model. The "PVS clear" material utilized to make the initial tooth impression also may be used to make the final impression of the tooth (which has been prepared for application of a restorative). It is noted that the "PVS monophase" material which is not transparent should not be used for the first impression as a clear impression material is required for light cure of the composite. The monophase material is very suitable for the second impression using the PVS die/base combination and also if the practitioner wants to use gypsum stone for the die in place of the PVS die/base combo. The monophase material is somewhat harder and less flexible than the clear material and so is more suited for the stone die.

According to a process of this invention, the PVS base 74 material is applied atop the PVS die 72 material. The PVS die 72 material may be injected through a syringe-like applicator that allows easy filling of deep areas in the cavities of the second impression. Alternatively, the PVS die 72 and PVS base 74 materials may be packed in auto-mix tubes that fit any standard impression gun. The PVS die 72 material must be sufficiently rigid so that it does not easily bend or distort under pressure, while the PVS base 74 is preferably a more viscous and more dense material that is similarly capable of withstanding pressure without bending or distorting.

Figure 3:
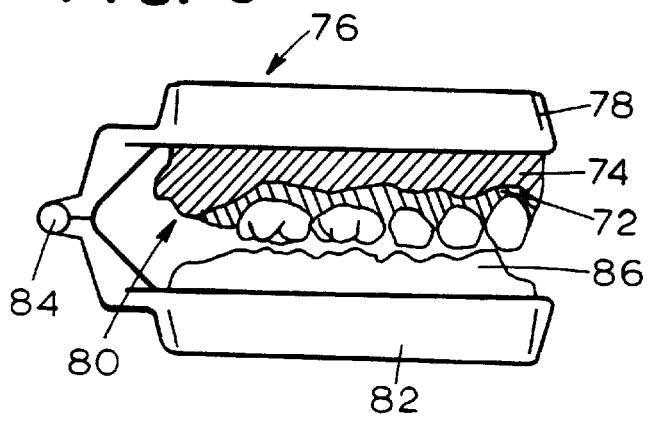
FIG. 3 is a side view of a base former and disposable articulator for use in a process according to the invention.
Figure 4:
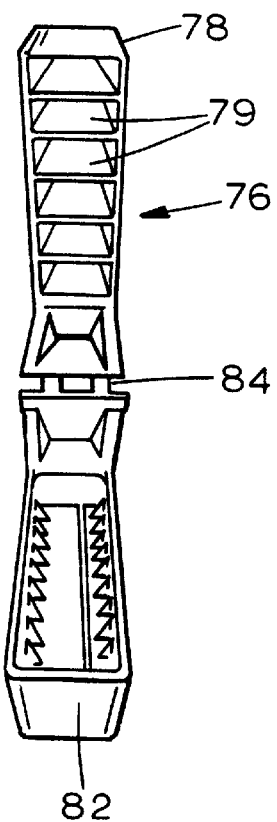
FIG. 4 is a front view of the base former and disposable articulator shown in FIG. 3.

FIG. 3 illustrates the two different impression materials, the PVS die 72, and the PVS base 74, indexed into the base former 78. FIG. 3 further illustrates the relative relationship between the PVS die 72, the PVS base 74, and index trays 79 of the base former 78. It is preferable that the PVS die material extends past the margin areas before the PVS base 74 material interferes with the PVS die 72. It is preferable that an amount of PVS base 74 be used such that there is created a positive seating of the PVS base 74 into the index trays 79. An entire die model 80 formed by the PVS die 72 and PVS base 74 according to a process of this invention is easily removable from the base former 78. FIG. 3 further shows the base former 78 as the top member (i.e., maxillary arch) of the base former/articulator 76 and a lower member (i.e., mandibular arch) 82. The top and lower members 78 and 82 are hinged by a hinge pin 84 as shown in FIG. 3 to afford a typical articulator character. The indexed trays 79 permit the individual removal of portions of the entire die model 80 formed by the PVS die 72 and PVS base 74 materials.

The die model 80 attached to the base former, as shown in FIG. 3, is matched to an opposing model 86 which is comprised of similar PVS base 74 or PVS die 72 materials or gypsum stone. If opposing crowns are to be fabricated, retention ridges which form the indexed trays 79 can be shortened in height to afford easier removal of the die model 80 from the particular member (i.e., top or lower member). The base former/articulator method provides a dentist with the ability to more accurately restore the subject teeth with proper occlusion. However, it is believed that the occlusion formed in the matrix material of the first impression will be very accurate, thus rendering the use of the base former/articulator optional.

Figure 5:
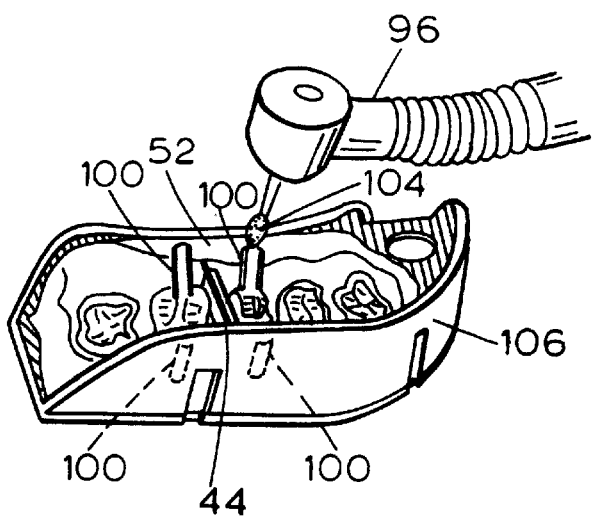
FIG. 5 is a perspective view of a tray containing material used in forming a second impression and the separator shown in FIG. 2 disposed therein.

The physical properties of the clear PVS matrix material used to make impressions allows vents to be cut therein that allow easy extrusion of a viscous composite used to fabricate the dental restoratives. As shown in FIG. 5, a high-speed drill 96 may be used to cut vertical vents 100 in buccal and lingual aspects of the matrix material 52. Preferably, an ultra-coarse diamond-shaped bur 104 is used to cut the vents 100. The vents 100 should be cut at least one mm deep and should extend from the gingival line of the cavity formed by the subject tooth to an edge of the tray 50, such as a tray flange 106. The clear PVS matrix material must be rigid and heat resistant, while not impeding or filling the bur 104 during the cutting of the vents 100. Conventional silicone materials either do not cut easily or end up in string-like fashion around the bur.

Figure 6:
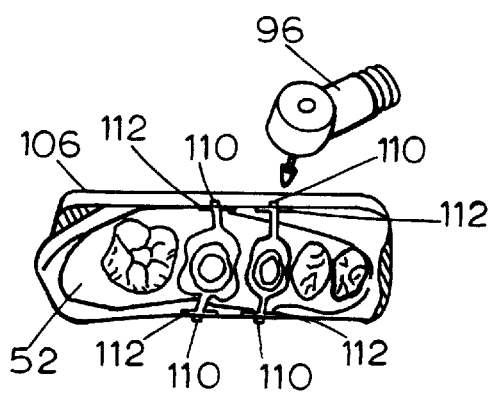
FIG. 6 is a top view of the tray shown in FIG. 5, which further illustrates the material and separator disposed therein.

Preferably the entire model die 80 is trial fitted to the clear PVS matrix material to ensure a seamless fit between the model 80 and matrix 52. If the fit is acceptable, vertical vents 110, as shown in FIG. 6, are cut in the die model corresponding to those that were cut into the clear PVS matrix material. The two vents 110, semi-circular in shape, are complimentary to each other and will form a full circle of approximately 2 mm in diameter. This vent size and shape may be adjusted to allow adequate extrusion of the viscous composite out of the die space during a subsequent press procedure to avoid any damage due to high pressure.

Horizontal vents 112 on the die model 80 are cut such that they intersect a corresponding vertical vent 110 and are approximately 2 mm from the tray flange 106. The horizontal vents 112 serve as a physical lock for the composite material to flow into as it extrudes out of the circular vents formed by the two semi-circles (vertical vents 110) of the die model 80 and the matrix material during the press procedure. The horizontal vents 112 are preferably the width of a football diamond bur and about 5 mm long. In other words, a horizontal vent 112 should intersect a vertical vent 110 and extend about 2–3 mm to the right and 2–3 mm to the left of the vertical vent 110 previously placed. At this time, a notch (not shown) is placed in a bottom surface of the PVS base to allow a tie 140 to be placed under and through the model. This allows the model to sit flat inside the curing apparatus.

Figure 7:
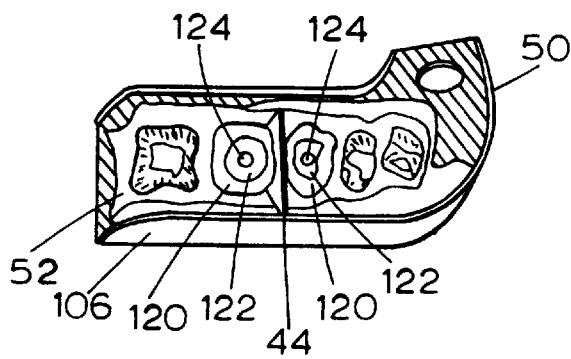
FIG. 7 is a top, perspective view of the tray shown in FIGS. 5 and 6, further showing layers of various composite materials used in a process according to the invention.
Figure 8:
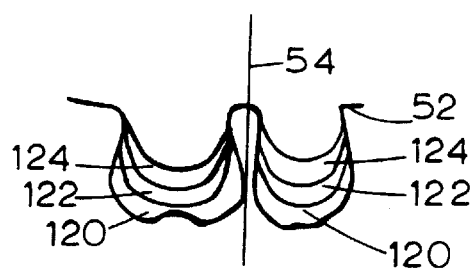
FIG. 8 is a side view of the various composite materials shown in FIG. 7.

FIGS. 7 and 8 illustrate various shades of composites selected to match the different colors expressed by different areas of the subject teeth. All teeth have multiple chromaticity and hues. Several different chromos of composite material packed into the crown with very gradual blend lines must be used to accurately depict a tooth crown. This is accomplished by beginning at the occlusal or incisal region of the clear matrix material. The first composite 120 will likely be a translucent incisal shade packed into the cusp tips and over the occlusal surface. This composite 120 is feathered over the buccal and lingual portions of the intaglio surface of the clear matrix material. Next, a body shade 122 is packed into the void and forms the majority of the packing material. A central hollow core is formed that will later accommodate the die when inserted into the clear matrix. The body pack is feathered toward the gingival region. The last composite 124 is typically a shade which will form the gingival aspect of the final restoration. The central hollow core is still preserved although it gets smaller with each subsequent layer. Once filled with the composite materials 120, 122, and 124, the clean matrix material is ready for the press of the die model 80.

Figure 9:
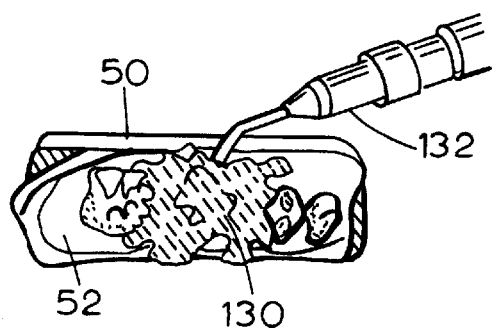
FIG. 9 is a top view of a clear matrix complex according to the invention showndaring a composite material application step according to a process of the invention, wherein a cavity formed by a subject tooth is filled with a composite material.

FIG. 9 shows a flowable dual-cure composite 130 being injected by a syringe 132 into the marginal areas of the preparations and the die model 80. This flowable composite 130 has a very low modulus of elasticity, and produces very accurate margins. The flowable composite 130 is also coated on the die to afford a good wetting of the surface and avoid bubbles in the more viscous body material. Another step according to a process of this invention is the placement of a small amount of the flowable composite 130 into the central core of the composite packing in the clear matrix material.

Figure 10:
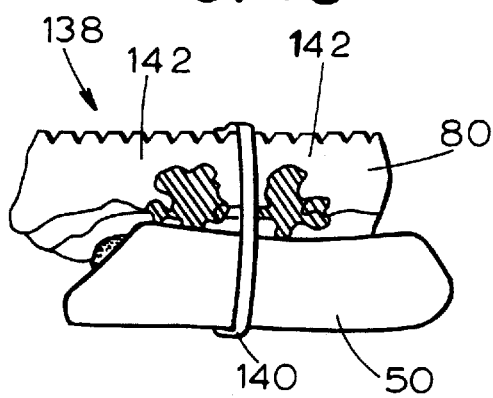
FIG. 10 is a side view of a model matrix complex during a molding step according to a process of the invention.
Figure 10A:
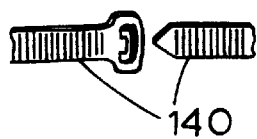
FIG. 10a is a front view of a tie shown in FIG. 10.

FIG. 10 shows a matrix model complex (MMC) 138 formed by the die model 80 and the clear matrix material 52. As shown in FIG. 10, the prepared teeth on the die model 80 are aligned with each corresponding central cavity created in clear matrix material 52 before pressing the die model 80 and clear matrix material 52 together, making sure that the interproximal separator 44 does not come into contact with (and thereby cutting) the PVS die. When the model 80 is pressed into the matrix 52, a slow but firm pressure is applied to each side of the MMC 138 causing the composite material 130 to flow and extrude down the vent holes. When the composite ceases to flow down the vents 110, the seating is complete, and the extruded composite is wiped into the horizontal vents 112 to assure a proper lock onto the die model 80. A tie 140, shown in FIGS. 10 and 10a, which is preferably clear, and made from nylon, or another heat-resistant material, may be looped around the MMC 138 and tightly secured by a wire tie gun (not shown) which has graduations on a tension scale that allow the dentist to meter the tension. A tension sufficient to hold the MMC 138 together without bending or distorting the clear impression tray 50 is preferred. The nylon tie shown in FIGS. 10 and 10a also can be hand tightened in lieu of using a wire tie gun.

If the buccal and/or lingual walls of the subject teeth have a relatively weak rigidity or are too flexible, the walls may become distorted during the preparation of the final composite material and result in an inaccurately shaped restoration. Therefore, a thin layer (e.g., 1 mm) of Aeliteflo composite material (Bisco, Inc. Schaumburg, Ill.) may be applied to coat the entire surface of the subject teeth. This layer of material can be quickly light cured. The layered subject teeth will exhibit increased rigidity and reduced flexibility.

Next, the MMC 138 is placed into a single curing apparatus according to the invention, generally 144 (shown in FIGS. 21–26 and discussed in detail, infra), for conducting a dual (light/heat) cure of the composite material 130, preferably under an oxygen-free gas (e.g., nitrogen or steam) pressure. The process steps associated with using the apparatus according to the invention also are discussed, infra.

After curing, the nylon tie 140 is cut and the clear matrix 52 is separated from the model 80. During this process, the restoration should remain intact on the model due to the locking nature of the cured material which flowed into the vents 110 and 112. The coronal surface is examined for any defects, and if needed, composite material is added to the model 80. The model 80 is then re-inserted into the clear matrix 52 and cured for one cycle. Once a satisfactory coronal finish is acquired, the restoration is removed from the model 80 by cutting off the composite material cured in the vents that lock the restorative onto the model 80.

Using a razor blade or knife, the PVS base 74 is sectioned from the model 80 by cutting completely through the model 80 and base. The model pieces can easily be realigned by inserting them back into the base former 78. Separating the base/model into individual pieces allows the margins to be trimmed and finished very accurately.

The fit of the restoration in the mouth, is checked and adjusted as needed, and then cemented with a luting cement such as one available under the trademark All-Bond C&B Luting Cement™ (Bisco, Inc., Schaumburg, Ill.).

Figure 11:
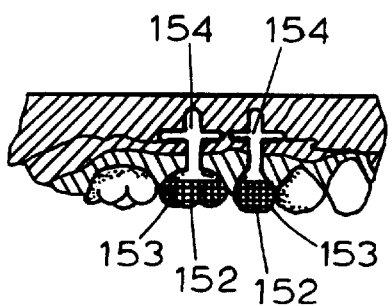
FIG. 11 is a side view of a model matrix complex according to the invention shown after a molding step according to a process of the invention.

FIG. 11 shows the final formed restorations 152. As discussed above and as shown in FIG. 11, any voids or imperfections present in the formed restorations 152 may be attended to by the addition of composite material 153 thereto and subsequent curing in the curing apparatus of the invention. When the restorations 152 are deemed adequate, the retention vents are removed from the die. Marginal finishing, refining of the occlusal anatomy, and polishing to achieve a high luster may be accomplished by methods known to a person of ordinary skill in the art.

Figure 12:
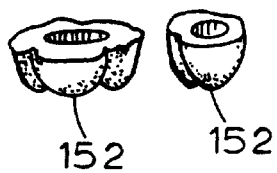
FIG. 12 is a perspective view of dental restoratives made according to a process of the invention.

FIG. 12 shows the formed restorations 152 ready for cementation. The intaglio surface is preferably micro-sandblasted using fifty-micron aluminum oxide and then acid treated with about 37% phosphoric acid. Silane is applied and blown dry. A suitable bonding agent, such as ONE-STEP™ (Bisco, Inc.) is painted inside the restoration and cemented to the tooth with wet-field bonding and dentin bonding primers such as PRIMERS A and B (Bisco, Inc.) or ONE-STEP™ (Bisco, Inc.). Any twenty-five-micron composite luting agent will suffice, such as C&B LUTING CEMENT (Bisco, Inc.). It is highly recommended that typical luting composites should be thinned with one drop of liquid catalyst for every one-quarter inch length of base used, thus, ensuring an adequately thin cement. The close tolerance of these restorations require the thinnest luting composites possible.

Processes according to the invention utilize restorative materials that are highly filled to resist abrasion and deformation while maintaining integrity of the margins. The final restoration is compatible with natural dentition and will not abrade opposing dentition or restorations. A variety of available shades ensures complete control of the aesthetics by the dentist. It is further advantageous that restorative materials used according to the invention may be added to or repaired in the mouth with light-cured composites. Proper surface treatment should be followed when adding composite to a previously place restoration.

It is noted that the restorations can be bonded with any dental adhesive and resin-luting cement, preferably a dual (light/self) cure resin cement.

Restoration materials used according to the invention provide more absorption of shock for implant prosthetics than traditional porcelain restorations. The composite restoration is not as brittle as porcelain and has similar radiopacity when viewed in radiographs. Due to the dense and highly polishable surface of the restorations, placing margins subgingivally (when dictated) does not promote inflammation. Since this restoration is bonded to the tooth, preparation of the subject tooth can be more conservative than with traditional restorative materials.

Figure 13:
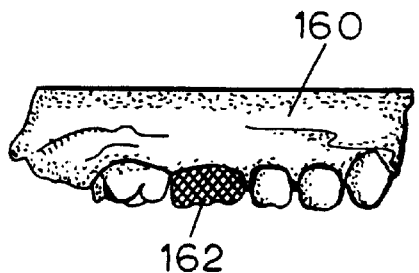
FIG. 13 is a perspective view of a model depicting a tooth that is missing a coronal finish.
Figure 14:
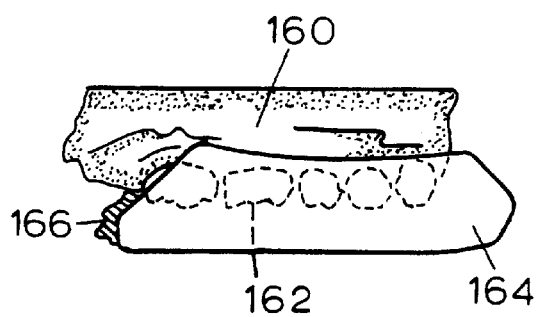
FIG. 14. is a perspective side view of tray as shown in FIGS. 1 and 5–7 containing material used to make an impression of the model shown in FIG. 13.

Another aspect of a process of the invention, illustrated in FIGS. 13–20 show a process for correcting a frequently-encountered dental condition of a tooth with intact roots but with missing coronal portions. In the illustrated case, a root canal has preserved all three roots of the right maxillary first molar (See FIG. 15). On the first patient visit, a wax-up is fabricated on a gypsum model that conforms to the outline for the residual root still apparent on the model. This wax-up will exactly duplicate the missing crown and will serve as a template for the crown to be fabricated with the techniques of the invention. FIGS. 13 and 14 also depict a model 160 including a wax facsimile tooth 162 generated by a dental technician (done between the first and second patient visits). During the first patient visit, maxillary and mandibular gypsum models are fabricated and used to create the wax coronal facsimile.

Once the wax facsimile tooth 162 is created, a tray 164 of a clear PVS matrix material 166 can be impressed with the gypsum model (FIG. 14). In the foregoing description of a process of making dental restoratives, such as a crown, intact clinical crowns allow the clear matrix material to be created intraorally. But in this case a very accurate gypsum study model is used to form the clear matrix. KY JELLY (Johnson & Johnson) is used to lubricate the gypsum model prior to seating the clear plastic tray 164 holding the clear PVS material 166, as shown in FIG. 14. This technique is performed in the same manner as in FIG. 1. Once set, the clear matrix material is trimmed away from the flanges and the impressed matrix material is set aside.

Figure 15:
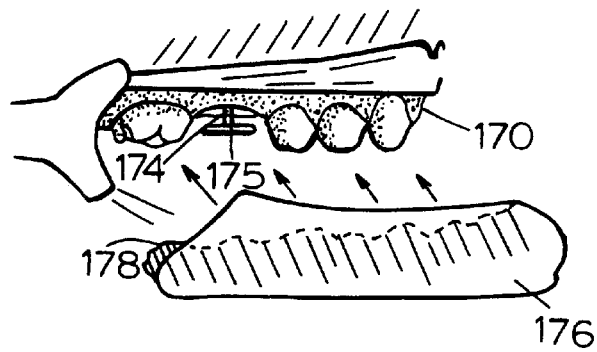
FIG. 15 is a perspective side view of the maxillary dental arch, further illustrating a group of teeth, wherein a post has been fitted to the lingual or palatal root canal of a missing tooth.

The next step is to generate a working PVS die model. FIG. 15 depicts an intra-oral arrangement 170 having the roots under the bone level. A palatal canal is prepared with special drills (not shown) that create the exact shape needed for a snug fit of a carbon-fiber post 174. The post 174 is trial-fitted into the prepared canal to verify that there is adequate exposure of the post 174 coronally to allow for the restoration to bond thereto. Preferably, the largest possible post should be used to ensure a maximum strength and retention. Over preparation of the canal walls should be avoided for fear of weakening the root. Carbon fiber posts 174 have been developed to eliminate the large post requirement associated with metal posts. However, it is still necessary to have a substantial size post where possible to afford as much surface adhesion to the composite as is possible. Even though carbon fiber does not require the mass that a cast gold post might, surface area for adhesion purposes remains an issue.

Figure 16:
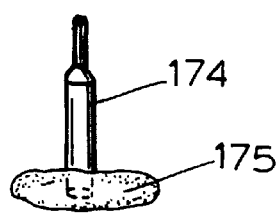
FIG. 16 is an enlarged, perspective view of the post shown in FIG. 15.

FIG. 16 illustrates a unique locking and orientation T-bar tab 175 created for the carbon fiber post 174. This allows the post to be picked up by the intraoral impression material and to provide proper orientation while the impression is injected with the PVS final impression material. Without the T-bar tab 175, it is difficult to make an impression. The T-bar retention tab 175, shown in FIG. 16 affords predictable retention. The T-bar 175 is created by injecting a strip of composite over the cut-end of the adjusted-to-length-post 174. A flowable composite, such as AELITEFLO™ (Bisco, Inc.) will do this faster than many other composites. In addition, the flowable composite wets the surface of the post and ensures absolute retention of the T-bar 175 and post 174. The T-bar 175 is created by laying the post 174 on a non-stick surface such as a mixing pad, injecting a substantial amount of composite over the cut end of the post 174, and overlapping the composite perpendicular to the major axis of the post 174.

Figure 17:
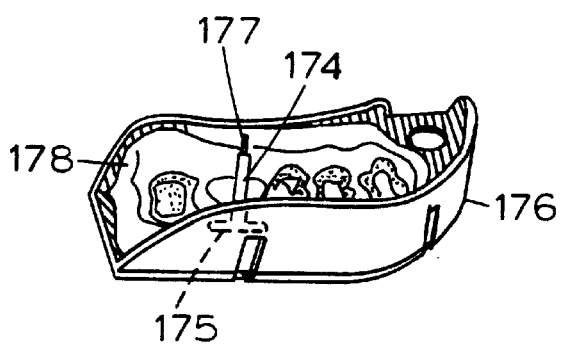
FIG. 17 is a perspective view of a tray containing material with an impression made therein by the teeth and post shown in FIG. 15.

With reference to FIG. 5, a clear tray 176 with a matrix material 178, similar to the matrix material 52 discussed herein with reference to FIG. 1, is placed against the subject teeth to form an impression. FIG. 17 shows the final impression ready for pour-up. The final impression is sprayed with a silicone mold release agent and then air dried for about five seconds. Preferably, the final impression is sprayed with two coats of the silicone mold release agent. The PVS die 72 material preferably is injected into the final impression while positioned on a lab vibrator. The impression tray 176 is loaded with the set impression material, the carbon fiber post 174 and T-Bar 175. A point 177 of the post 174 preferably had been inserted deep in the root canal space prior to removing the final impression from the mouth.

Figure 18:
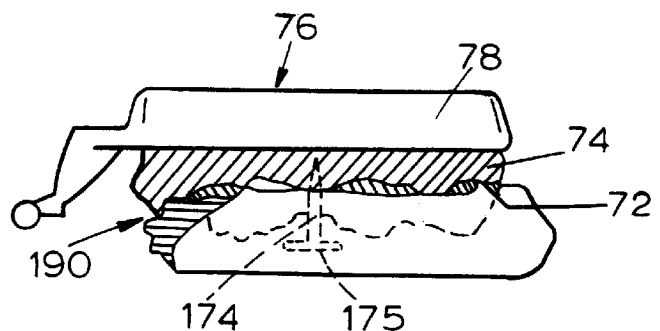
FIG. 18 is a perspective view of another process of making dental restoratives according to the invention.

FIG. 18 depicts the final impression injected with the PVS die 72 material and connected to the base former/articulator 76 with the flexible PVS base 74 material. Upon separating, this will serve as a model 190 for an MMC 192 (shown separated in FIG. 19), ready to be pressed with composite as already described with respect to FIGS. 1–11 herein. With careful inspection, the dentist will find an extremely accurate marginal replication of the residual root system and the hole created by the post and adjacent teeth of the same arch replicated in great detail. The clear matrix and the die are vented as previously described herein and shown in FIG. 5.

A carbon fiber post 195 is cut to the adjusted length so that it will be completely covered in the mass of coronal composite. The cut end of the post should be no closer than 2 mm to the final occlusal surface. The exposed portion of the post should be lightly sandblasted using fifty-micron aluminum oxide and coated with a resin bonding agent. The coating should be light cured. The post is then inserted into the PVS die model and checked for proper fit. The die model is then trial fitted into the clear matrix and checked to ensure a seamless interface between the two.

Figure 19:
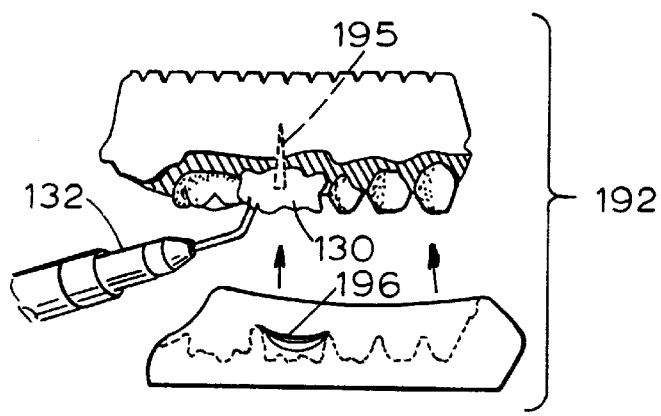
FIG. 19 is a side view of a post coated with a composite material used according to a process of the invention.
Figure 19A:
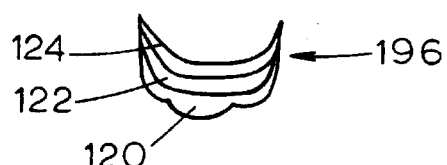

FIG. 19 shows the post 195 coated with a dual (light/heat) cured composite 130 and the margins injected with the same flowable material. Preferably, the post 195 was covered before inserting it into the canal of the die. After inserting the post 195, any exposed portion is covered with more of the dual-cure flowable composite. At the point in time of the process shown in FIG. 19, the clear matrix has been packed with composite making up a restoration 196 as previously described herein with respect to FIGS. 7 and 8 and also shown in FIG. 19a. The die model is now pressed into the clear matrix loaded with composite. Slow but firm pressure is applied until material ceases to flow out the vents. Excess composite is wiped into the horizontal locking vent and a wire tie is secured around the MMC 192.

The MMC 192 is placed into the curing apparatus 144. Upon completion of the cycle a wire tie (not shown) holding the MMC together is cut and removed. If careful inspection of the coronal portion reveals no voids in the material, the vents (as described herein with respect to FIGS. 5, 6, and 11) may be separated and the restoration 196 removed from the die. If composite must be added to the restoration, the MMC is then run through another curing cycle in the curing apparatus 144. This second cycle can be run without using the clear matrix. Subsequently, the intaglio (underside) surface of the restoration 196 is inspected for voids or tackiness. This surface should be free of an oxygen-inhibited layer. If voids need to be filled, such may be performed by filling with composite and reinserting the restoration 196 back onto the die. The restoration may be locked onto the die using a light cured composite and extending the composite from the composite crown down to the locking vents to ensure a proper orientation of the restoration on the die. The composite-filled vents may be cured before placing in the curing apparatus 144. Once placed back into the curing apparatus 144, an abbreviated cycle may be used since it is unlikely that any light will reach the bottom of the restoration.

Figure 20:
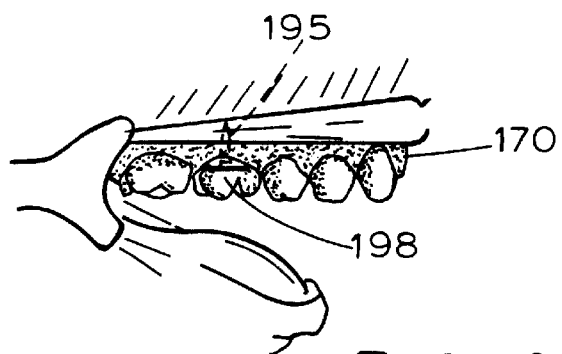
FIG. 20 is a side view of a dental restorative and post as attached to the maxillary dental arch.

After corrections are made, the restoration 196 is removed from the die model and all margins are finished to exact status. The coronal portion is finished and polished to form a finished restorative 198 as shown in FIG. 20.

The canal is prepared with about 37% phosphoric acid as is the remaining tooth structure. A primer for wet-field bonding, such as PRIMERS A & B (Bisco, Inc.) is coated into the canal and air dried to evaporate any volatile. The surface is then coated with a thin layer of PRE-BOND (Bisco, Inc.) to prevent premature setting of the self-cure luting cement.

The intaglio surface of the restoration is sandblasted, as is the exposed surface of the post. Phosphoric acid is applied for 10 seconds and rinsed thoroughly. The surface is then dried and coated with silane. A thin layer of ONE-STEP (Bisco, Inc.) resin bonding agent is then added and the surface is then blown dry of all volatiles on the surface. Any thin luting composite, for example, C&B LUTING COMPOSITE (Bisco, Inc.) can be used for cementation of the post-crown restoration. This luting agent is injected into the canal using a CENTRIX needle tube (product #290031; Centrix Direct, Shelton Conn.), and also coats the intaglio surface of the restoration at this time. The restoration is then seated on the prepared tooth ensuring the post is aligned toward the opening of the canal. The restoration is firmly seated with a gentle rocking motion (buccal to lingual motion) to help extrude excess cement. Once fully seated, any excess cement is wiped from the margins. The margins are then light cured for one full minute on the buccal and lingual surfaces. The dentist can now release the gingivally-applied pressure to the restoration after light curing. With the margins cured, the restoration will not move and be stable while the self cure mechanism achieves final polymerization. Occlusion is now adjusted using an ultrafine diamond and 30-flute finishing burs. A final polish is easily achieved using diamond paste.

A preferred curing apparatus 144 according to the invention is a programmable oven for curing dual (light/heat) cure dental composites as well as many other single (e.g., light, heat or self-cured) curable materials. The curing apparatus 144 also provides for curing under pressure, while eliminating the presence of oxygen and its inhibition effects.

Specifically, FIGS. 21–25 show one embodiment of a curing apparatus 144 having a housing 200 which defines a curing chamber 202 and a dome chamber 203, a base 204 which includes a curing platform 206, a holding platform 208 and a control panel 210. The apparatus also includes a curing lamp 211 disposed in the dome chamber and a lock-down mechanism 212 for securing the housing 200 to the curing platform 206. In the embodiment illustrated in the figures, the platform 206 is generally cylindrical in shape and the housing 200 has a domed structure. However, it is noted that other housing geometries are possible, including a rectangular housing.

Cooperating with the lock-down mechanism 212 is a pressure sealing gasket 214 which is mounted on a rim 216 integral to and encircling a flat surface 217 of the curing platform 206. The gasket makes contact with the rim 216 and with a bottom surface 218 of the housing 200 during the curing operation of the apparatus to ensure an air-tight environment in the curing chamber 202 when it is desired to perform pressurization of the chamber. As shown in the drawing figures, the pressure sealing gasket 214 is designed such that it is removable. The gasket 214 includes a vertically extending flange 220 in contact with the rim 216 and a horizontally extending flange 222 in contact with a horizontal flange 224 of the curing platform 206. The gasket 214 may be made from polyester, or other flexible, heat-resistant materials. Preferably, the gasket is clear or semi-clear, allowing an operator to determine if the curing lamp 211 is shining. An additional, flat, annular gasket (not shown) may be inserted beneath the gasket 214 in a recess of a flange 224 of the curing platform 206 to provide further cushioning and sealing of the platform 206 with the housing 200 during operation of the apparatus 144.

Figure 23:
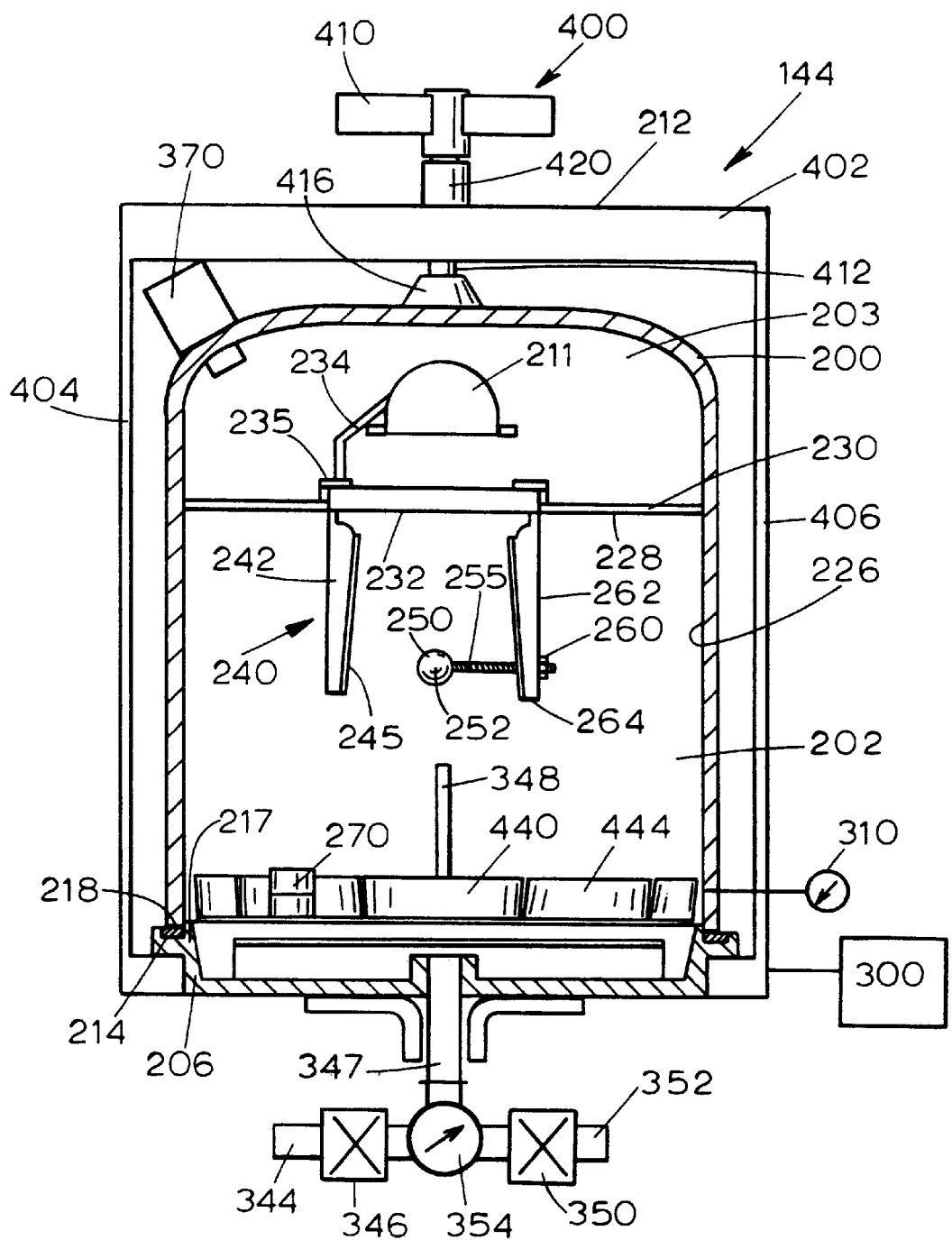
FIG. 23 is a cross-sectional and partially diagrammatic view of the apparatus shown in FIG. 21.

With reference to FIG. 23, the housing 200 and the curing platform 206 define the curing chamber 202. More specifically, the curing chamber is defined by the flat surface 217 of the curing platform 206, an inner cylindrical surface 226 of the housing 200 and a surface 228 of a separator wall 230 which includes a transparent glass window 232, preferably having insulation capabilities (e.g., borosilicate glass). A gasket (not shown) is located between the window 232 and the curing chamber wall 230 to act as an air and heat seal between the window 232 and the curing chamber wall 230.

The lamp 211 located in the dome chamber 203 is mounted on an arm 234 which is attached to a mounting fixture 235 which in turn is attached to the separator wall 230 and the window 232. The lamp 211 is oriented with respect to the wall 230 to allow the lamp 211 to shine through the window 232 to irradiate and heat the curing chamber 202. The lamp 211 preferably is a 250–300 watt curing lamp (visible output) which provides for improved heating rates. Preferably, a 300 watt lamp is utilized which has a smooth surface parabolic reflector. The curing lamp 211 is sufficient for radiation (infrared) cure of a composite. However, it is noted that separate heating coils also may be employed in addition to the curing lamp 211.

Within the curing chamber 202 there is a temperature intensity gradient minimizing system, generally 240 which includes a hollow, substantially cylindrical shroud 242 having an inner liner 245, and a ball 250 positioned centrally within the shroud. The ball is preferably made of brass and preferably has an aperture 252 extending therethrough. The ball 250 is attached to the shroud 242 by a horizontally extending shaft 255 with a connector 260. The shaft 255 shown in FIG. 23 is threaded and extends through an aperture in the shroud 242. The connector 260 is a nut which is threaded on the shaft and abuts an outer surface 262 of the shroud 242.

The inner liner 245 is either a coating or a thin liner material which covers an inner surface 262 of the shroud 242. The inner surface 262 may be cylindrical in shape, or as shown in FIG. 23, slightly cone-shaped, flaring outwardly toward an end 264 of the shroud 242. The inner liner 245 may be a light-colored coating, or lining material, such as paper. In the embodiment shown in FIG. 23, the liner 245 is made from yellow paper.

While not necessary to the success of the invention, the curing temperature can be controlled by a sensor 270 using a thermister (for example, a bead thermister Model TS 104-169 supplied by Oven Industries, Inc., Mechanicsburg, Pa.) disposed in the curing chamber 202 in an environment similar to what the material to be cured is exposed to. For example, with respect to FIGS. 23, 24 and 25, the sensor 270 is a floor-mount, fixed location sensor using a black bead thermister 272 having a bead portion (not shown) imbedded at a depth of one mm into a cylindrical core portion 274. The core portion 274 is made from an untinted composite resin material (AELITE WEAR from Bisco, Inc.) composite resin material, used for dental restorations. The composite for the core portion 274 was chosen because it does not yellow with repeated heat cycling to 125 degrees C. In the embodiment shown in FIG. 25, the core portion 274 is about 4.6 mm long and has a diameter of about 6 mm. The bead portion (not shown) of the thermister 272 is disposed about 1 mm from an end 275 of the sensor 270 and substantially centrally, with respect to an outer circumference of the core portion 274.

A portion of the thermister 272 comprising leads 276 which are attached to the bead (not shown) is embedded into a second cylindrical core portion 278 which is made from a PVS die 72 material. The remainder of the thermister leads 276 and a two-pronged receptical 280 fitted to the thermister leads 276 are disposed in a chamber 282 defined by a hollow cylindrical housing 284 made from one or more types of PVS. In the embodiment shown in FIG. 25, the cylindrical core portions 274 and 278 and the thermister leads 276 are surrounded by an outer cylindrical portion 286 made from the PVS die 72 material already discussed herein. In the embodiment shown in FIG. 25, the outer cylindrical portion 286 has an outer diameter of about 14 mm and a length of about 9.7 mm.

Adjacent to the cylindrical portion 286 and surrounding the two-prong receptical 280 is an outer cylindrical portion 288 made from the PVS base 74 material discussed previously herein. In the embodiment shown in FIG. 25, the outer cylindrical portion 288 has an outer diameter of about 14 mm and a length of about 11 mm. It is noted that the sensor assembly materials need not be limited to that shown in FIG. 25. Many materials may be used for the sensor, including ceramics.

The prongs of the two-prong receptical 280 extend through and are stabilized by a base 290 made from a sufficiently rigid, non-conducting, heat-insensitive polymeric material. A cylindrical cap 292 of the PVS base 74 material surrounds the base 290, the prongs of the two-prong receptical 280 extending through the cap 292. The two-prong receptical 280 is mated with a two-prong plug 294 mounted in the curing platform 206 and extending upwardly from the flat surface 217.

The entire sensor assembly 270 is sealed and subjected to pressure cycling. Therefore, two vents 296 are drilled in the cylindrical portion 288 that extend between the chamber 282 and an outer surface 298 of the cylindrical portion 288.

The sensor plug 294 is connected to a microprocessor 300 which is preferably located in the base 204 of the apparatus 144. The sensor 270 thus reads the temperature via the microprocessor 300. Once a desired target temperature or light cure exposure time is reached, the lamp 211 is controlled. The sensor 270 and associated plug 294 are preferably located on the flat surface 217 of the curing platform 206 at a location near a perifery 302 of a curing area 304 of the curing chamber 202. With respect to the embodiment shown in FIG. 24, the sensor 270 is located at a distance of about 30 mm left of a center 306 of the curing platform 206. Temperature in the curing chamber 202 may be observed by viewing a temperature indicator 310.

An optional sensor assembly, generally 320 for another embodiment according to the invention is shown in FIGS. 24, 26 and 27. A sensor 321 is not directly attached to a base plug 294 mounted on the curing platform 206, but rather has leads 276' attachable by a user to two stationary poles 322 and 324. The poles 322 and 324 cooperate with a thermister (not shown) embedded in a composite core 274' and outer cylindrical portion 286' made of PVS die material, similar to the sensor 270. Thus, the elements 274', 276', 278' and 286' are the same or similar to (with the exception of dimensions) to the elements 274, 276, 278, and 286 discussed herein with respect to FIG. 25. As shown in FIG. 27, because the leads 276' attach directly to the poles 322 and 324, the sensor 321 does not include the two-prong receptical 280, the cylindrical portion 288 made from the PVS base material, the base 290 or the PVS cap 292 shown in FIG. 25. Because the poles 322 and 324 are connected to the sensor 321 by the lead lines 276', the sensor 321 may be placed at any desired location within the curing chamber 202. (As shown in FIG. 27, discussed in detail, infra, the sensor leads 321 are fed through a slot 466 of a tray 460, allowing for placement of the sensor 321 on a planar surface 462). Preferably, the poles 322 and 324 include spring-loaded connectors which clamp onto the wire lead lines 276'. The poles 322 and 324 are connected to the microprocessor 300 and thus read the temperature via the microprocessor 300. Once a desired target temperature is reached, the lamp and/or heating elements 211 are/is controlled via feedback of the sensor attached to the poles 322 and 324.

It is noted that the sensor (270 or 321) is most preferably approximately the same height as the restoration in the die. It also may be desirable to place a thin layer of clear PVS material over the sensor to simulate the insulation that the clear matrix provides over the restoration.

A pressurized inert gas environment may be created in the curing chamber 202 by passing pressurized inert gas, such as nitrogen, from a gas source (not shown) through an inlet line 344 and a control valve 346 and then through a conduit 347 connected to a tube 348 mounted on the curing platform 206 and extending upwardly from the flat surface 217. The nitrogen pressure within the curing chamber 202 may be further controlled by a separate air purge passageway connected to an outlet valve 350, which permits the flow of gas through an outlet line 352. Nitrogen pressure is monitored using an internal pressure reading gauge 354 shown in FIGS. 21 and 22 and schematically in FIG. 23.

As previously noted, inert gas used with the apparatus is not limited to nitrogen. Argon, steam, or any other relatively inert gas or mixtures of gases with relatively low oxygen level, and preferably substantially free of molecular oxygen, can be utilized. However, nitrogen is well-suited for use in the invention because of its ease of use, availability, and low cost.

As previously described herein, the curing lamp 211 is disposed in the dome chamber 203. The temperature of the hollow dome chamber 203 is maintained by an air multiplier 370 which is attached to the housing 200 defining the dome chamber 203. The air multiplier is an advantageous feature of the invention as the dome temperature rises whenever the curing lamp 211 is operating. If the lamp 211 is operating for extended time periods, high temperatures in the dome chamber 203 may harm wiring insulation and other temperature sensitive materials in the dome chamber 203. Therefore, cooling air is fed through the hollow dome chamber 203 by the air multiplier 370 which is attached to a conduit 372 which in turn is attached to a source of pressurized air (not shown), controllable by a valve mechanism (not shown), preferably mounted on the base 204 and being equipped with a pressure guage (not shown). The air multiplier 370 cools by taking advantage of the Cowanda Effect (venturi-like effect). Air multipliers 370 suitable for use in the invention are manufactured by EXAIR (Cincinnati, Ohio). Dome chamber temperatures are typically maintained below 90 degrees C. and preferably below 75 degrees C. Typical cooling air pressures range from about 40 psi to about 100 psi (60 psi is preferred). When using one air multiplier, the pressure is preferably about 60 psi. Air flows through and out of the dome chamber 203 through a plurality of vents 380. Each of the vents 380 extends between the chamber 204 and an outer surface 382 of the housing 200.

The dome chamber 203 temperature is preferably monitored by microprocessor controlled thermisters, for example, thermisters supplied by Oven Industries, Inc. A conduit 385 extending between the dome portion of the housing 200 and the base 204 houses lines for connecting such thermisters to the microprocessor 300. The conduit 385 also houses a power line for the air multiplier 370. Cooling of the dome chamber 203 may also be accomplished by convection.

Also attached to the housing 200 defining the dome chamber 203 is a handle 390 which extends from the outer surface 382 of the dome housing. The handle 390 is used to lift the housing 200 (and apparatus disposed in the dome and curing chambers) for movement between the curing platform 206 and the holding platform 208.

The lock-down mechanism 212, which is pivotally attached to the curing platform 206, forms an air-tight environment within the curing apparatus 144 unit when pressure purging is desired. The lock-down mechanism 212 includes a clamping assembly, generally 400 and frame portions 402, 404 and 406. The clamping assembly 400 includes a threaded bolt 408 attached to a winged handle 410 at one end thereof and having a rounded surface 412 at the other end thereof. The rounded surface 412 is sized to fit within a depression 414 defined by a nub 416 attached to a top-most portion of the surface 382 of the housing 200 defining the dome chamber 206. The bolt 408 extends through a threaded aperture disposed in the frame portion 402. The frame portion 402 extends between and is attached to the parallel frame portions 404 and 406. A washer 420 (which is not threaded) is disposed about the bolt and is between the handle 410 and the frame portion 402. Each of the frame portions 404 and 406 has an aperture through which a bolt 422 extends, hingably attaching the frame portion to the curing platform 206. Preferably, the frame portions 404 and 406 extend into apertures located on a surface 425 of the base 204, the apertures having a length so as to allow for movement of the clamping assembly 400 from a vertical position (i.e., the frame portions 404 and 406 being vertical) and a position in which the frame portions 404 and 406 abut against a base surfaces defining such apertures wherein the frame portions 404 and 406 are approximately between 30 degrees and 45 degrees from the vertical, providing ample space for a user to place the housing 200 on the curing platform 206. When the apparatus is to be operated, the clamping assembly 400 is pivoted so that the frame portions 404 and 406 are in a substantially vertical position and the handle 410 is rotated, moving the threaded bolt downwardly with the rounded surface 412 disposed in the depression 414 and in contact with the nub 416, pressing the housing 200 downwardly, sealing the housing 200 to the curing platform 206.

The clamping assembly may include a micro-positioning sensor to assure that the frame members 404 and 406 are in exact vertical position for safety purposes. A very small rotation from vertical (few mm) and the apparatus will neither pressurize nor heat. The clamping assembly may also be made to move forward, backward or from right to left, depending upon the orientation and geometry of the housing of the curing apparatus.

Figure 22:
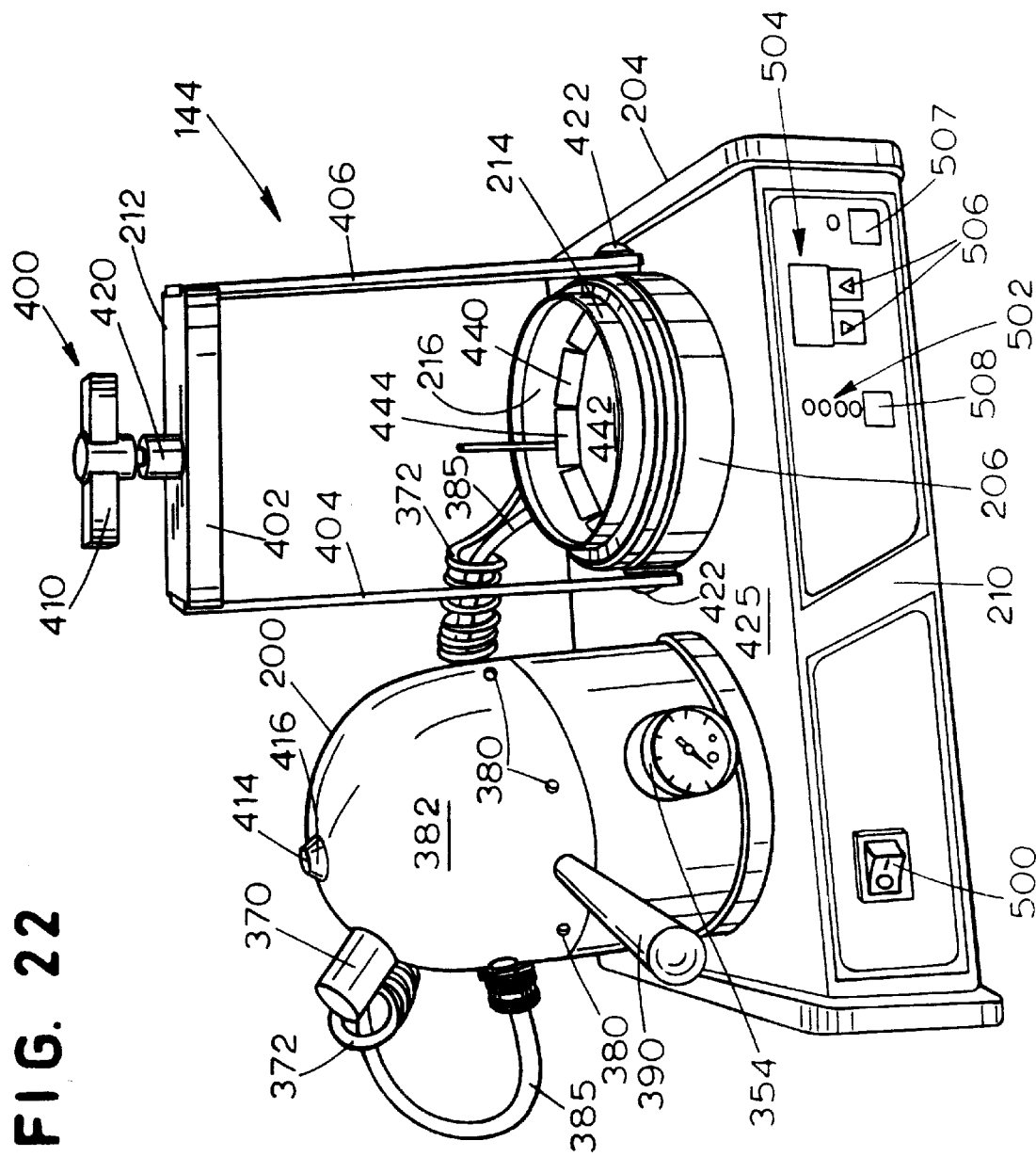
FIG. 22 is a perspective view of the apparatus of FIG. 21 shown in a second, non-operating position.

A sample tray 440 for use in the inventive apparatus and process is shown in FIGS. 22, 23 and 24. The tray 440 includes a flat surface 442 and side walls 444. Materials to be cured are placed on the flat surface 442. The tray 440 includes an aperture 446 through which the plug 294 extends. In the embodiment shown in FIG. 24, the side walls 444 are made by making evenly spaced triangular cuts 448 in a piece of sheet metal, followed by bending the wall portions created by the cuts, resulting in a tray with a flat bottom surface 442 and eight side walls 444. The tray advantageously substantially covers the platform surface 217, while providing space between the rim 216 and the side walls 444 so as not to interfere with the tube 348 used for nitrogen purging. As shown in FIG. 24, the tray 440 also may include a cut-out 450 for placement of the sensor poles 322 and 324.

A second sample tray 460 for use in the inventive apparatus and process is shown in FIG. 27. The tray includes a substantially planar portion 462 and side walls 464 which are perpendicular to the planar portion 462. The portion 462 includes slots 466. The planar portion 462 may either be placed on the flat surface 217 of the curing platform 206 with a sample surrounded by the side wall 464, or inverted so that pins 468 of a standard stone tooth mold 470 often used in dental labs, can be inserted through the slots 466. With the tray 460, multiple tooth molds can be placed in the slots 466. As discussed herein, supra, the sensor 321 may be placed at any desired location on the planar portion 462, with the lead lines 276' extending through one of the slots 466. (In FIG. 27, the sensor 321 is shown spaced from the tray 460 in order to show that the lead lines 276' are extending through one of the slots 466.)

It is noted that the sample tray 440 also may be inverted for use in the curing chamber 202. The lead lines 276' of the sensor 321 may be fed through the aperture 446 and then connected to the poles 322 and 324.

Figure 21:
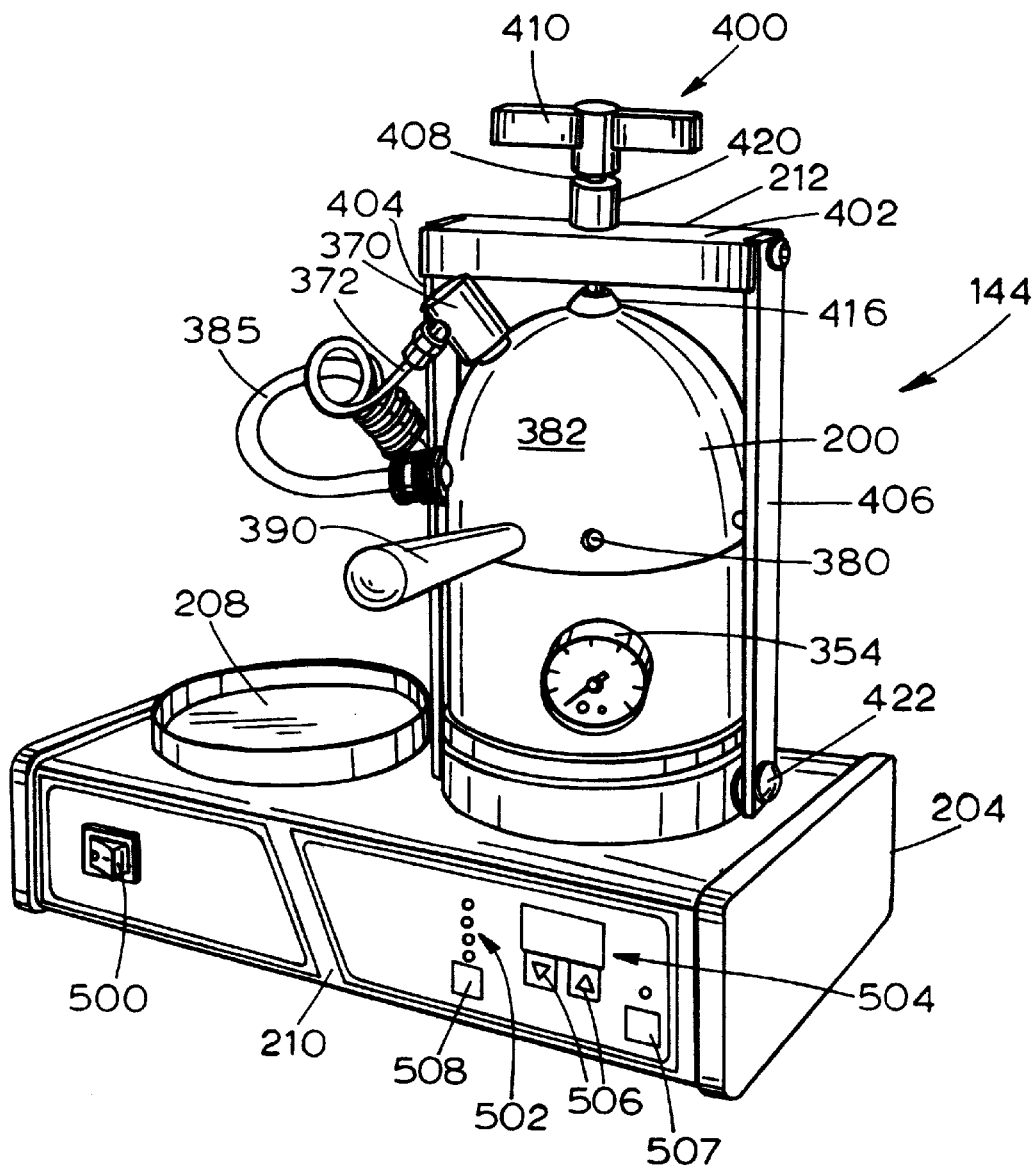
FIG. 21 is a perspective view of one embodiment an apparatus according to the invention shown in a first, operating position.

FIGS. 21 and 22 show the control panel 210 of an electronic control system (not shown) that is used to operate the curing apparatus 144. The control panel 210 includes an on/off switch 500 and lighted indicators 502 which inform the user whether the apparatus is undergoing pressure purge, curing, cooling, or if the process is completed. A display 504 (such as an LED display) allows the user to set a "soak" time for the material to be cured using up/down arrows 506. The "soak" time is the amount of time the samples are to remain in the apparatus after the sensor (270 or 320) indicates that a pre-set target temperature has been reached within the composite (274 or 274') in the sensor. All other functions of the apparatus 144, such as the target temperature, number of pressure purges, cool down time, cooling air pressure and pressure are pre-programmed. To set the "soak" time, a user must first press the "set time" button 507, followed by the up/down arrows 506. A user begins the curing process by pressing a start button 508.

In a typical procedure for curing a composite material using the curing apparatus 144, the housing 200 is moved to the holding platform 208 as shown in FIG. 22. A sample to be cured is placed onto the sample holding tray 440 and the tray is placed on the flat surface 217 of the curing platform 206. The housing 200 is then placed on the curing platform 206 and the clamping assembly 400 is pivoted to a position wherein the frame members 404 and 406 are substantially vertical as shown in FIG. 21. The handle 410 is turned until the rounded surface 412 is fully seated in the depression 414 of the nub 416 to form an air-tight environment within the curing chamber 202. Next, the "soak" time is selected by first pressing the button 507, followed by the arrows 506. The acceptable "soak" times range between zero and ten minutes, with 0.5 minute increments. The start button 508 is then pressed to initiate the curing cycle.

Upon depressing the start button 508, the system will purge the curing chamber 202 for a pre-programmed number of cycles (usually from about 4–10), where, for example, a single purge cycle consists of pressurization of the curing chamber 202 with air, for example, pressurized from about 60 psi to about 90 psi, and then depressurization. Following the final pressurization the display lights 502 will indicate that the curing apparatus 144 is in the curing stage. Following curing of the sample, the curing chamber 202 will depressurize. According to an embodiment of the invention, at any given time during the curing cycle, the control panel 210 and the displays thereon provide information as whether the apparatus is in an initial heating mode, the "soak" mode, or cooling down. Similar information may be collected and displayed using a computer.

A typical pre-programmed cycle (with the exception of "soak" time) includes:

a. Six pressure purges of the curing chamber 202 to remove the oxygen-inhibiting environment, each of which consists of pressurizing the chamber to between about 55 and about 80 psi followed by depressurization (each purge typically takes about fifteen seconds);

b. maintaining a minimum pressure of about 60 psi for the remainder of the curing cycle (the first stage of the sixth purge preferably is held until the end of the heat-soak period);

c. curing lamp operation to a sensor target temperature of about 125 degrees C.;

d. "soak" operation at 125 degrees C. for the amount of time set by the operator (variation of temperature over all of the curing surface 217 should not exceed target temperature plus/minus 5 degrees C.; bandwidth equal to 2.5 C. total width) and maintaining the nitrogen pressure throughout the "soak" operation;

e. maintaining a cooling air pressure in the dome chamber 203 of about 50 p.s.i. throughout operation of the apparatus 144; and f. allowing the curing chamber 202 to vent nitrogen and begin cooling for about five minutes upon completion of the cycle.

Safety features of the apparatus 144 may include pressure transducers controlled by the system microprocessor 300. The transducers can be used to monitor inert gas or steam line and cooling air line pressures. If pressures are insufficiently low, system software can detect them, and safely shut the system down, warning the user of a problem. Also, a safety blow-out valve may be provided if the pressure goes beyond a safe limit. A thermister (not shown) located in the dome may be used to read dome temperature and shut down the heating lamp if the dome temperature exceeds a certain maximum temperature.

The curing apparatus 144 of the invention can be modified to simultaneously cure multiple MMCs. A large curing apparatus 144 might be employed in a dental lab to accommodate the large number of orders they commonly receive. Dental labs may also utilize a computer link possibility for processor control and/or data logging purposes, such as information on sample type or types, dates, customer name, specific cure specifications, and any other pertinent information for a specific job. Furthermore, specially designed multiple sample holders (for curing multiple jobs) may be used so as to improve efficiency of the apparatus. Such holders would either fit singly on a stage in a side-by-side or stackable formation. Furthermore, stacking devices may be utilized.

EXAMPLE 1

Crown Technique

1. Make pre-operative matrix with clear PVS Material in a clear impression tray. If restoring multiple, adjacent crowns place 0.001 (inch) interproximal separators between teeth where restorations will meet each other.
2. Prepare subject tooth for partial or full coverage utilizing less-parallel wall retention form (5–15 degree convergence) than for a cast gold design.
3. Pack retention cord, take impression with PVS, reversible hydrocolloid or a two (2) part alginate material.
4. Inject PVS die material into final impression. PVS final impressions require 2 coats of mold release, then air syringe dry for 5 sec. Hydrocolloid/alginates do not require mold release.
5. Inject PVS base material on top of die material, fill index tray and seat on top of die/base pour-up. This forms the indexing system.
6. Cut vertical vents in the clear matrix extending from mid buccal and lingual areas (below prep) to flange extension.
7. Trial fit clear matrix over die model. Interface of the two materials should be seamless (no air gaps). Mark the position of the buccal/lingual vents onto the die model. Create vent on die model with sharp instrument and extend vent as far up the die as possible.
8. Extend both vents up to the preparation margin. About 5 mm below prep margin, place a horizontal vent that intersects the vertical vent. This will provide retention of the restoration upon curing.
9. Lubricate the restoration area of the clear matrix with unfilled resin such as FORTIFY (Bisco, Inc.).
10. Into the clear matrix, pack composite(s) in layers, feathering the materials from cusp tips to margins to blend different shades of composite. Create a central core area while packing to allow a path of insertion of die.
11. Inject flowable composite, such as AELITEFLO (Bisco, Inc.), onto the margins of the die and proceed to cover the die itself with a thin coat. Add composite to each vent on the die model and the clear matrix.
12. Fit clear matrix over die model (this will be called the model-matrix-complex, or MMC) and secure with nylon tie. Place in the curing apparatus.
13. Select "soak" time. Push start button.
14. Remove nylon tie, cut vents to release restoration, finish margins, polish and trial fit in the mouth. Checks occlusion and inter-proximal contacts.
15. Cement restoration with a universal bonding agent, such as ONE-STEP™, and a dual cure cement such as C&B™ LUTING CEMENT, both products of Bisco, Inc.

EXAMPLE 2

Samples were cured with a 50 watt bulb at 60 psi with 6 purges of nitrogen. The 6 purges has eliminated the oxygen inhibition problem completely. There was only one sample of each.

| Time of Cure | Strength in MPa |
| --- | --- |
| 3 minutes | 29.12 MPa |
| 4 minutes | 52.60 MPa |
| 5 minutes | 50.31 MPa |

Samples were cured with a 65 watt bulb at 60 psi with 6 purges for 2, 3, 4, and 5 minutes. There was only one sample each.

| Time of Cure | Strength in MPa |
| --- | --- |
| 2 minutes | 45.07 MPa |
| 3 minutes | 38.91 MPa |
| 4 minutes | 50.49 MPa |
| 5 minutes | 55.87 MPa |

The highest wattage bulb provided the best curing, resulting in the manufacture of the apparatus 141 which has a 250–300 watt curing lamp.

The following procedures have been conceived and tested utilizing method steps according to the invention:
1. Single Crowns;
2. Multiple adjacent crowns utilizing special 0.001 interproximal stainless steel separators incorporated into the special clear matrix at pre-op impression;
3. Inlays;
4. Single and multiple onlays adjacent to each other;
5. Single visit, 15 minute removable, claspless temporary partial dentures;
6. Single visit, 15 minute claspless orthodontic retainers;
7. Carbon fiber, full ferrule, composite posts in a single visit;
8. Carbon fiber movebloc post/crown combinations done in a single visit;
9. Denture occlusion to test varying vertical dimensions and occlusion schemes;
10. Long term, full arch, fixed temporary restorations for full mouth reconstruction;
11. In-office progressive loading occlusal addition technique for healing implant;
12. Acid-etch bridges reinforced with carbon fiber for support;
13. Orthodontic fixed one tooth space maintainers to replace unsightly bonded loop devices, performed in a single visit;
14. Laminate veneers done in a single visit;
15. One visit cosmetic periodontal splints reinforced with carbon fiber bans;
16. Single crowns with I.C. attachments for partial dentures in a single visit; and
17. Crown to a partial in a single visit.

Overall, the processes of the invention are far less expensive than traditional methods since indirect restoration procedures can be completed in a single visit to the dental office, eliminating the requirement for a minimum of two patient visits. Tooth impressions and models are prepared quickly, inexpensively, and with high accuracy and precision using polyvinyl siloxane (PVS) materials. Furthermore, composite restorations prepared according to the invention show very high strength and excellent wear resistance. This is due to the fact that the apparatus 144 provides a heat curing cycle which achieves a higher degree of monomer conversion in the final restoration. Additionally, when using a process according to the invention, all polymerization shrinkage resulting from curing occurs extra-orally and can be compensated for during the cementation of the restoration. Any space between model and tooth created by shrinkage will be filled by the resin-luting agent when finally cemented in the mouth. This significantly increases the chance for a successful, permanent restoration.

Procedures according to the invention allow for a more productive use of chair time. Once properly trained, dental assistants can easily master this technique since it is very similar to fabricating custom, temporary restorations. The additional time to oven-cure and finish this restoration is more than offset by the time savings in not having to see the patient back for the second visit required by most indirect processes. The time to cement the finished restoration is approximately that required to cement a temporary restoration.

Furthermore, according to the invention, tacky and hazy composite surfaces caused by oxygen inhibition during the light-curing step are not formed since curing is performed under an inert nitrogen atmosphere. Thus, surface finishes are superior. This procedure eliminates the need to shape and contour the anatomy of the restoration with a handpiece since a preoperative impression recreates the original occlusal morphology, interproximal contacts and axial contours. External and internal defects in the composite, due to bubbles, are minimized since curing is done under pressure. These defects can decrease overall restoration strength and wear characteristics.

Also according to the invention, better quality removable prosthetic temporary devices (also known as stay plates or flippers) may be fabricated in the office during one office visit. Performed according to processes of the invention, the fabrication of the temporary device would not require clasps. Repairs, additions or modifications of such devices can be easily accomplished chair-side.

Custom composite posts with full-ferrule design that satisfy the prosthodontist who will not use pre-formed dowel posts made of metal or carbon fiber also may be prepared according to the invention. A carbon-fiber post may be inserted into the root canal and incorporated into an impression. A T-bar locking tab is created at the top of a C-Post to ensure a secure relationship in the impression material. Any typical light-cured composite such as AELITEFLO Bisco, Inc.) can be used to make the T-bar on the C-Post. This impression is poured with relatively low viscosity polyvinyl siloxane (PVS) rigid model-making material and the base of the model is poured with a PVS material of higher viscosity which will ultimately have greater flexibility than the model PVS. After separation of the fully cured model from the impression, the exposed C-Post can be incorporated into a mass of composite that will form the coronal portion of the post. A full ferrule can be created at the gingival aspect to prevent root fracture. The restoration is left on the model and placed in the curing apparatus of the invention and cured using both light and thermal curing. The color of this prosthesis will allow the practitioner to place all-glass restorations without opaquing. This is not possible with full-ferrule gold posts.

Also according to the invention, periodontally compromised teeth that require splinting can now be corrected indirectly, thereby assuring lab-quality prostheses with a single-visit procedure and no lab expenses. Splints may be fabricated using existing polyethylene or fiberglass reinforced ribbons or tapes covered with a composite and then placed in the curing apparatus 141 for curing. These are long-term restorations and can be reinforced with carbon fiber bars. This will replace costly lab-produced crown and inlay type splints that require a second cementation visit, temporary restorations, and all of the concomitant setup and cleanup with the cementation visit. The curing apparatus of the invention eliminates the lab expenses and the revenueless second visit.

Processes and apparatus of the invention may also be used to increase the vertical dimension (material to be applied over the occlusal surfaces and cured) on a denture. Performed according to the invention, adding composite to the denture results in a highly dense and smooth surface comfortable to the patient during the period the dentist evaluates vertical dimension. If more height is required, it is simply added to the existing material and oven-cured. Such material will last for months to years.

Processes and apparatus of the invention may also be utilized in the progressive loading of implants during a tissue-healing stage, which historically has been a laboratory process involving multiple patient visits. During progressive loading procedures, the hardness of the occlusal materials on implant-borne crowns or bridges is gradually increased so that undue stresses on the healing tissue are avoided. The processes of the invention will allow the dentist to make hardness changes of the occlusal materials in his or her office by simply grinding off a layer of composite and adding a softer or harder composite to the freshly ground occlusal area. Clear matrix stents (0.020 inches) can be used to load the new material and form the occlusion, which is then cured in the curing apparatus of the invention. These stents can be made from a very exact wax-up of the implant area. This technique allows very precise occlusion, with varying composite hardness, to properly load the healing implant over a period of time. The curing apparatus of the invention will allow the dentist to have complete control of the progressive loading phase, thereby ensuring predictability of the process.

A further process utilizing apparatus and methods according to the invention is the injection of a flexible composite monobloc post and core that mimics exactly the dentin color of the tooth. When dentin is so dark from necrosis of the pulp tissue, it is desirable to remove that portion of the crown. In the past, the coronal portion could only be recreated with a cast gold post and core. The gold color then had to be opaqued out with ceramic in order to use any of the new, all glass non-metal restorations like Empress or OPC. Carbon fiber use addressed that issue in processes according to the invention, but still did suffice for the situation where the root canal was too thin for a carbon fiber post to be inserted. There are also practitioners who prefer to not use carbon fibers but rather injectable composite reinforced with RIBBOND (Ribbond, Seattle, Wash.) or some such fiber. The problem with these is that the entire system had to be injected intra-orally and heat treatment could not be used. By using the processes according to the invention, the operator prepares his root canal with a special drill and very narrow post system (e.g., Union Broach). The post is T-barred for retention on top so it will come out of the canal with the impression. The impression is next injected with a new metal-filled PVS (e.g., Titanium) that will transmit heat to the deepest aspects of the root canal space in the die mode. The post space is injected with a special flexible, flowable dual-cure (light/heat) composite and very narrow strips of RIBBOND or GLASSPAN (Glasspan, Exton, Pa.) reinforcements are packed into the mass. The mass of the root canal is made continuous with the coronal portion which is a highly viscous, flowable material that is shaded to various dentin colors. This monobloc prosthesis is now light and heat cured under nitrogen pressure in the curing apparatus. The heat conducting PVS die will allow easy separation of the post and core.

Another material that can be used is a flexible, injectable post material that has glass fibers or similar reinforcing materials in it. The metal-filled die material and injectable post composite with and without glass fibers allow the practitioner the freedom to use metal-less glass crowns. The overall process can be done chair-side, in the dentist's office.

The foregoing detailed description is given for clearness of understanding only, and no unnecessary limitations should be understood therefrom, as modifications within the scope of the invention will be apparent to those skilled in the art.

We claim:

1. A process for fabricating an indirect dental restorative comprising the sequential steps of:
    (a) forming a first, pre-operative impression of a tooth to be restored using a first polyvinyl silicone (PVS) material disposed in a clear tray;
    (b) forming a final post-operative impression of the tooth in a second PVS material and allowing the material to dry;
    (c) pouring a low viscosity third PVS material into the final impression, the third material forming a model tooth;
    (d) applying a fourth PVS material onto the third PVS material, the fourth material having a viscosity higher than the viscosity of the third material, the fourth material providing a base for the model tooth;
    (e) removing the model tooth and base from the final impression;
    (f) fitting the model tooth into the pre-operative impression made from the first PVS material;
    (g) applying composite material to the pre-operative impression;
    (h) inserting the model tooth into the composite-containing pre-operative impression, forming a matrix; and
    (i) curing the composite in the matrix in a single apparatus for conducting one of light, heat, or both light and heat cure of the dental composite.

2. The process of claim 1 comprising the following steps subsequent to step (f) and before step (g):
    (1) making a substantially vertical trough on the buccal and lingual sides of the model tooth;
    (2) removing the model tooth and base from the pre-operative impression;
    (3) extending the vertical troughs into the base material; and
    (4) making a substantially horizontal trough crossing through the vertical trough.

3. The process of claim 1 comprising the step of applying a suitable release agent to the dry PVS material forming the final impression subsequent to step (b) and before step (c).

4. The process of claim 1 wherein step (i) is performed in an oxygen-free, pressurized environment.

5. The process of claim 4 wherein the oxygen-free, pressurized environment comprises an inert gas.

6. The process of claim 4 wherein the oxygen-free, pressurized environment comprises steam.

7. The process of claim 4 wherein the oxygen-free, pressurized environment comprises water.

8. The process of claim 1 wherein the first PVS material is clear and has a viscosity of between about 500,000 cps and about 600,000 cps.

9. The process of claim 1 wherein the second PVS material is a monophase material having a viscosity of between about 400,000 cps and about 450,000 cps.

10. The process of claim 1 wherein the third PVS material has a viscosity of between about 20,000 cps and about 30,000 cps.

11. The process of claim 1 wherein the fourth PVS material has a viscosity of between about 350,000 cps and about 450,000 cps.

12. The process of claim 1 wherein the composite material comprises a resin, at least one inorganic filler, a polymerization reaction initiator to initiate light cure, an amine accelerator, and at least one thermal catalyst to initiate thermal cure.

13. The process of claim 12 wherein the resin comprises at least one reactive methacrylate functionalized monomer or oligomer selected from the group consisting of 2-hydroxyethyl methacrylate (HEMA), ethylene glycol dimethacrylate (EGDMA), diethyleneglycol dimethacrylate (DEGDMA), triethylene glycol dimethacrylate (TEGDMA), tetrahydrofurfuryl methacrylate, trimethylolpropane trimethacrylate (TMPTMA), 2,2-bis[4(2-hydroxy-3-methacryloxypropoxy)phenyl]propane (bis-GMA), urethane dimethacrylate (UDMA), diphenyl sulfone dimethacrylate, polytetramethyleneglycol dimethacrylate PTMGDMA), and mixtures thereof.

14. The process of claim 12 wherein the filler is selected from the group consisting of barium aluminum silicate, barium oxide, lithium aluminum silicate, strontium, lanthanum, tantalum, glass, quartz, silica, fused silica, colloidal silica, alumina, zirconia, tin oxide, and mixtures thereof.

15. The process of claim 12 wherein the polymerization reaction initiator to initiate light cure is selected from the group consisting of camphorquinone, benzil, biacetyl, 9,10-phenanthrenequinone, naphthoquinone and mixtures thereof.

16. The process of claim 12 wherein the amine accelerator is selected from the group consisting of tripropylamine, N-alkyldialkanolamine, tryalkanolamine, and acrylate or methacrylate derivatives thereof.

17. The process of claim 12 wherein the thermal catalyst is selected from the group consisting of benzoyl peroxide, t-butyl perbenzoate, and 1,1-di(tert-butylperoxy)-3,3,5-trimethylcyclohexane.

18. The process of claim 12 wherein the composite material further comprises pigments, tints, and stabilizers.

19. The process of claim 1 wherein the step of applying composite material to the pre-operative impression comprises the application of several layers of composite, each of a different shade to produce a restorative having multiple chromaticity and hues similar to a tooth.

20. The process of claim 1 wherein step (i) further comprises providing a curing apparatus having at least one temperature sensor comprising a thermister disposed in a material substantially similar to at least one component of the composite material applied in step (g).

21. The process of claim 20 comprising heating the matrix to a target temperature indicated by the thermister disposed in the chamber.

22. The process of claim 21 further comprising heating the matrix for a set time after the thermister has reached the target temperature.

23. A process for fabricating an indirect dental restorative comprising the steps of:
(a) forming a dental restorative of a first composite material comprising a resin, said resin comprising at least one reactive methacrylate functionalized monomer or oligomer selected from the group consisting of 2-hydroxyethyl methacrylate (HEMA), ethylene glycol dimethacrylate (EGDMA), diethyleneglycol dimethacrylate (DEGDMA), triethylene glycol dimethacrylate (TEGDMA), tetrahydrofurfuryl methacrylate, trimethylolpropane trimethacrylate (TMPTMA), 2,2-bis[4(2-hydroxy-3-methacryloxypropoxy)phenyl]propane (bis-GMA), urethane dimethacrylate (UDMA), diphenyl sulfone dimethacrylate, polytetramethyleneglycol dimethacrylate (PTMGDMA), and mixtures thereof;
(b) providing a curing apparatus having a curing chamber, a curing lamp, and a temperature sensor assembly comprising a thermister disposed in a second composite material, the thermister being connected to a control device for operating the curing lamp, the second composite material comprising a resin having at least one reactive methacrylate functionalized monomer or oligomer selected from the group consisting of 2-hydroxyethyl methacrylate (HEMA), ethylene glycol dimethacrylate (EGDMA), diethyleneglycol dimethacrylate (DEGDMA), triethylene glycol dimethacrylate (TEGDMA), tetrahydrofurfuryl methacrylate, trimethylolpropane trimethacrylate (TMPTMA), 2,2-bis[4(2-hydroxy-3-methacryloxypropoxy)phenyl]propane (bis-GMA), urethane dimethacrylate (UDMA), diphenyl sulfone dimethacrylate, polytetramethyleneglycol dimethacrylate (PTMGDMA), and mixtures thereof; and
(c) heating the restorative in the curing apparatus to a target temperature indicated by the thermister disposed in the second composite.

24. The process of claim 23 further comprising heating the restorative for a set time after the thermister has reached the target temperature.

25. An apparatus for fabricating a dental restorative comprising:
(a) a curing chamber for curing a first mass of a composite material;
(b) a curing lamp;
(c) a temperature sensor assembly disposed in a second mass of a composite material in the curing chamber; and
(d) a device for controlling temperature connected to the temperature sensor assembly and the curing lamp.

26. The apparatus of claim 25 wherein the temperature sensor assembly comprises a thermister disposed in said second mass of composite material.

27. The apparatus of claim 26 further comprising means for minimizing temperature intensity gradients in the curing chamber.

28. The apparatus of claim 27 wherein the means for minimizing temperature intensity gradients in the curing chamber comprises a shroud for directing the electromagnetic radiation emitted by said curing lamp and a ball having an aperture for dispersing said electromagnetic radiation throughout the curing chamber.

29. The apparatus of claim 25 wherein the first mass and second mass are the same composite material.

30. The apparatus of claim 25 wherein the composite material comprises a resin having at least one reactive methacrylate functionalized monomer or oligomer selected from the group consisting of 2-hydroxyethyl methacrylate (HEMA), ethylene glycol dimethacrylate (EGDMA), diethyleneglycol dimethacrylate (DEGDMA), triethylene glycol dimethacrylate (TEGDMA), tetrahydrofurfuryl methacrylate, trimethylolpropane trimethacrylate (TMPTMA), 2,2-bis[4(2-hydroxy-3-methacryloxypropoxy)phenyl]propane (bis-GMA), urethane dimethacrylate (UDMA), diphenyl sulfone dimethacrylate, polytetramethyleneglycol dimethacrylate (PTMGDMA), and mixtures thereof.

31. The apparatus of claim 25 wherein the composite material is surrounded by a PVS material.

32. The apparatus of claim 25 wherein the curing lamp is located in a dome chamber that is separated from said curing chamber by a wall having a transparent glass window.

33. The apparatus of claim 32 further comprising an air multiplier for supplying cooling air to said dome chamber.

34. The apparatus of claim 32 wherein the temperature of said dome chamber is monitored by microprocessor-controlled thermistors.

35. An apparatus for fabricating a dental restorative comprising:
(a) a curing chamber;
(b) a curing lamp;
(c) a temperature sensor assembly comprising a thermister disposed in a composite material in the curing chamber wherein the composite material comprises a resin having at least one reactive methacrylate functionalized monomer or oligomer selected from the group consisting of 2-hydroxyethyl methacrylate (HEMA), ethylene glycol dimethacrylate (EGDMA), diethyleneglycol dimethacrylate (DEGDMA), triethylene glycol dimethacrylate (TEGDMA), tetrahydrofurfuryl methacrylate, trimethylolpropane trimethacrylate (TMPTMA), 2,2-bis[4(2-hydroxy-3-methacryloxypropoxy)phenyl]propane (bis-GMA), urethane dimethacrylate (UDMA), diphenyl sulfone dimethacrylate, polytetramethyleneglycol dimethacrylate (PTMGDMA), and mixtures thereof; and
(d) a device for controlling temperature connected to the temperature sensor assembly and the curing lamp.

36. An apparatus for fabricating a dental restorative comprising:
(a) a curing chamber:
(b) a curing lamp;
(c) a temperature sensor assembly comprising a thermister disposed in a composite material wherein the composite material is surrounded by a PVS material; and
(d) a device for controlling temperature connected to the temperature sensor assembly and the curing lamp.

* * * * *